(12) United States Patent
Song

(10) Patent No.: US 9,402,637 B2
(45) Date of Patent: Aug. 2, 2016

(54) CUSTOMIZED ARTHROPLASTY CUTTING GUIDES AND SURGICAL METHODS USING THE SAME

(71) Applicant: Howmedica Osteonics Corporation, Mahwah, NJ (US)

(72) Inventor: Keun Song, Palo Alto, CA (US)

(73) Assignee: Howmedica Osteonics Corporation, Mahwah, NJ (US)

(*) Notice: Subject to any disclaimer, the term of this patent is extended or adjusted under 35 U.S.C. 154(b) by 388 days.

(21) Appl. No.: 13/749,095

(22) Filed: Jan. 24, 2013

(65) Prior Publication Data

US 2014/0107655 A1 Apr. 17, 2014

Related U.S. Application Data

(60) Provisional application No. 61/712,577, filed on Oct. 11, 2012.

(51) Int. Cl.
| | |
|---|---|
| A61B 17/58 | (2006.01) |
| A61B 17/60 | (2006.01) |
| A61F 2/00 | (2006.01) |
| A61B 17/15 | (2006.01) |
| A61B 17/56 | (2006.01) |

(52) U.S. Cl.
CPC ......... *A61B 17/157* (2013.01); *A61B 2017/568* (2013.01)

(58) Field of Classification Search
CPC .............. A61B 17/154; A61B 17/157; A61B 2017/568; A61B 17/155; A61B 17/1764; A61B 2019/508; A61B 2017/00526; Y10T 409/30084

USPC .................. 606/79, 80, 82, 86 R–88, 90
See application file for complete search history.

(56) References Cited

U.S. PATENT DOCUMENTS

| | | |
|---|---|---|
| 3,195,411 A | 7/1965 | MacDonald et al. |
| 3,825,151 A | 7/1974 | Arnaud |

(Continued)

FOREIGN PATENT DOCUMENTS

| | | |
|---|---|---|
| DE | 3305237 A1 | 8/1983 |
| DE | 102005023028 A1 | 11/2006 |

(Continued)

OTHER PUBLICATIONS

U.S. Appl. No. 14/272,147, filed May 7, 2014, Park et al.

(Continued)

*Primary Examiner* — Christopher Beccia
*Assistant Examiner* — Diana S Jones
(74) *Attorney, Agent, or Firm* — Polsinelli PC

(57) ABSTRACT

Implementations described and claimed herein provide an arthroplasty system for making resections in a patient knee. In one implementation, the system includes a femoral cutting guide having a patient specific mating region, and a distal planar surface distally spaced from a distal resection surface based on thicknesses of femoral and tibial implants. The distal planar surface may be used to check ligament balance. The system further includes a tibial cutting guide having a patient specific mating region and a an anchor pin hole intersecting with a proximal resection slot near a medial or lateral edge of the proximal resection slot. The anchor pin hole being configured to receive an anchor pin that may serve as a sawing stop during a proximal resection.

10 Claims, 19 Drawing Sheets

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,517,969 A | 5/1985 | Halcomb et al. |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A | 7/1991 | Coates |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,098,436 A | 3/1992 | Ferrante et al. |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A | 2/1994 | Lackey |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| 5,514,140 A | 5/1996 | Lackey |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A | 5/1998 | Haines et al. |
| 5,768,134 A | 6/1998 | Swaelens et al. |
| 5,769,092 A | 6/1998 | Williamson, Jr. |
| 5,769,859 A | 6/1998 | Dorsey |
| 5,798,924 A | 8/1998 | Eufinger et al. |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia, III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Roble et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |

(56) References Cited

U.S. PATENT DOCUMENTS

| | | |
|---|---|---|
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,203,628 B1 | 4/2007 | St. Ville |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,373,286 B2 | 5/2008 | Nikolskiy et al. |
| 7,383,164 B2 | 6/2008 | Aram et al. |
| 7,388,972 B2 | 6/2008 | Kitson |
| 7,392,076 B2 | 6/2008 | de La Barrera |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,548,638 B2 | 6/2009 | Graessner |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,621,744 B2 | 11/2009 | Massoud |
| 7,621,920 B2 | 11/2009 | Claypool et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,641,663 B2 | 1/2010 | Hodorek |
| 7,643,862 B2 | 1/2010 | Schoenefeld |
| 7,658,741 B2 | 2/2010 | Claypool et al. |
| 7,660,623 B2 | 2/2010 | Hunter et al. |
| 7,682,398 B2 | 3/2010 | Croxton et al. |
| 7,693,321 B2 | 4/2010 | Lehtonen-Krause |
| 7,695,520 B2 | 4/2010 | Metzger et al. |
| 7,699,847 B2 | 4/2010 | Sheldon et al. |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,769,429 B2 | 8/2010 | Hu |
| 7,780,672 B2 | 8/2010 | Metzger et al. |
| 7,780,681 B2 | 8/2010 | Sarin et al. |
| 7,787,932 B2 | 8/2010 | Vilsmeier et al. |
| 7,794,467 B2 | 9/2010 | McGinley et al. |
| 7,796,791 B2 | 9/2010 | Tsougarakis et al. |
| 7,799,077 B2 | 9/2010 | Lang et al. |
| D626,234 S | 10/2010 | Otto et al. |
| 7,806,838 B2 | 10/2010 | Tsai et al. |
| 7,806,896 B1 | 10/2010 | Bonutti |
| 7,815,645 B2 | 10/2010 | Haines |
| 7,824,181 B2 | 11/2010 | Sers |
| 7,842,039 B2 | 11/2010 | Hodorek et al. |
| 7,842,092 B2 | 11/2010 | Otto et al. |
| 7,881,768 B2 | 2/2011 | Lang et al. |
| 7,894,650 B2 | 2/2011 | Weng et al. |
| 7,927,335 B2 | 4/2011 | Deffenbaugh et al. |
| 7,935,150 B2 | 5/2011 | Carignan et al. |
| 7,940,974 B2 | 5/2011 | Skinner et al. |
| 7,950,924 B2 | 5/2011 | Brajnovic |
| 7,963,968 B2 | 6/2011 | Dees, Jr. |
| 7,967,868 B2 | 6/2011 | White et al. |
| D642,263 S | 7/2011 | Park |
| 7,974,677 B2 | 7/2011 | Mire et al. |
| 7,981,158 B2 | 7/2011 | Fitz et al. |
| D642,689 S | 8/2011 | Gannoe et al. |
| 8,007,448 B2 | 8/2011 | Moctezuma de La Barrera |
| 8,021,368 B2 | 9/2011 | Haines |
| 8,036,729 B2 | 10/2011 | Lang et al. |
| 8,052,623 B2 | 11/2011 | Haimerl et al. |
| 8,059,878 B2 | 11/2011 | Feilkas et al. |
| 8,062,302 B2 | 11/2011 | Lang et al. |
| 8,066,708 B2 | 11/2011 | Lang et al. |
| D651,315 S | 12/2011 | Bertoni et al. |
| 8,073,521 B2 | 12/2011 | Liew et al. |
| 8,077,950 B2 | 12/2011 | Tsougarakis et al. |
| 8,083,745 B2 | 12/2011 | Lang et al. |
| 8,086,336 B2 | 12/2011 | Christensen |
| 8,092,465 B2 | 1/2012 | Metzger et al. |
| 8,105,330 B2 | 1/2012 | Fitz et al. |
| D655,008 S | 2/2012 | Gannoe et al. |
| 8,112,142 B2 | 2/2012 | Alexander et al. |
| 8,115,485 B1 | 2/2012 | Maier et al. |
| 8,122,582 B2 | 2/2012 | Burdulis, Jr. et al. |
| 8,126,234 B1 | 2/2012 | Edwards et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,152,855 B2 | 4/2012 | Tulkis et al. |
| 8,160,345 B2 | 4/2012 | Pavlovskaia et al. |
| 8,165,657 B2 | 4/2012 | Krueger |
| 8,167,888 B2 | 5/2012 | Steffensmeier |
| 8,170,641 B2 | 5/2012 | Belcher |
| 8,170,716 B2 | 5/2012 | Coste-Maniere et al. |
| 8,175,683 B2 | 5/2012 | Roose |
| 8,177,850 B2 | 5/2012 | Rudan et al. |
| D661,808 S | 6/2012 | Kang |
| 8,202,324 B2 | 6/2012 | Meulink et al. |
| 8,206,153 B2 | 6/2012 | Berckmans, III et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,730 B2 | 9/2012 | Alexander et al. |
| 8,265,949 B2 | 9/2012 | Haddad |
| 8,282,646 B2 | 10/2012 | Schoenefeld et al. |
| 8,290,564 B2 | 10/2012 | Lang et al. |
| 8,306,601 B2 | 11/2012 | Lang et al. |
| 8,311,306 B2 | 11/2012 | Pavlovskaia et al. |
| D672,038 S | 12/2012 | Frey |
| 8,323,288 B2 | 12/2012 | Zajac |
| 8,331,634 B2 | 12/2012 | Barth et al. |
| 8,337,501 B2 | 12/2012 | Fitz et al. |
| 8,377,066 B2 | 2/2013 | Katrana et al. |
| 8,398,646 B2 | 3/2013 | Metzger et al. |
| 8,407,067 B2 | 3/2013 | Uthgenannt et al. |
| 8,460,302 B2 | 6/2013 | Park et al. |
| 8,460,303 B2 | 6/2013 | Park |
| 8,480,679 B2 | 7/2013 | Park |
| 8,483,469 B2 | 7/2013 | Pavlovskaia et al. |
| 8,532,361 B2 | 9/2013 | Pavlovskaia et al. |

(56) References Cited

U.S. PATENT DOCUMENTS

| | | | |
|---|---|---|---|
| D691,719 S | 10/2013 | Park | |
| 8,545,509 B2 | 10/2013 | Park et al. | |
| 8,617,171 B2 | 12/2013 | Park et al. | |
| 8,617,175 B2 | 12/2013 | Park et al. | |
| 8,734,455 B2 | 5/2014 | Park et al. | |
| 8,737,700 B2 | 5/2014 | Park et al. | |
| 8,777,875 B2 | 7/2014 | Park | |
| 8,777,955 B2 | 7/2014 | Park | |
| 8,801,719 B2 | 8/2014 | Park et al. | |
| 8,801,720 B2 | 8/2014 | Park et al. | |
| 8,828,011 B2 | 9/2014 | Park et al. | |
| 8,882,779 B2 | 11/2014 | Park et al. | |
| 8,961,527 B2 | 2/2015 | Park | |
| 8,968,320 B2 | 3/2015 | Park et al. | |
| 2002/0160337 A1 | 10/2002 | Klein et al. | |
| 2003/0009167 A1 | 1/2003 | Wozencroft | |
| 2003/0055502 A1 | 3/2003 | Lang et al. | |
| 2004/0102792 A1 | 5/2004 | Sarin et al. | |
| 2004/0102866 A1 | 5/2004 | Harris et al. | |
| 2004/0133276 A1 | 7/2004 | Lang et al. | |
| 2004/0147927 A1 | 7/2004 | Tsougarakis et al. | |
| 2004/0153066 A1 | 8/2004 | Coon et al. | |
| 2004/0153087 A1* | 8/2004 | Sanford et al. | 606/88 |
| 2004/0204760 A1 | 10/2004 | Fitz et al. | |
| 2004/0220583 A1 | 11/2004 | Pieczynski, II et al. | |
| 2004/0243148 A1 | 12/2004 | Wasielewski | |
| 2004/0243481 A1 | 12/2004 | Bradbury et al. | |
| 2005/0054914 A1 | 3/2005 | Duerk et al. | |
| 2005/0059978 A1 | 3/2005 | Sherry et al. | |
| 2005/0065617 A1 | 3/2005 | de la Barrera et al. | |
| 2005/0080426 A1 | 4/2005 | Qian | |
| 2005/0149091 A1 | 7/2005 | Tanamal et al. | |
| 2005/0192588 A1 | 9/2005 | Garcia | |
| 2005/0245934 A1 | 11/2005 | Tuke et al. | |
| 2005/0245936 A1 | 11/2005 | Tuke et al. | |
| 2005/0256389 A1 | 11/2005 | Koga et al. | |
| 2005/0267584 A1 | 12/2005 | Burdulis, Jr. et al. | |
| 2005/0272998 A1 | 12/2005 | Diehl et al. | |
| 2006/0015018 A1 | 1/2006 | Jutras et al. | |
| 2006/0015030 A1 | 1/2006 | Poulin et al. | |
| 2006/0015188 A1 | 1/2006 | Grimes | |
| 2006/0079755 A1 | 4/2006 | Stazzone et al. | |
| 2006/0110017 A1 | 5/2006 | Tsai et al. | |
| 2006/0122491 A1 | 6/2006 | Murray et al. | |
| 2006/0155293 A1 | 7/2006 | McGinley et al. | |
| 2006/0155294 A1 | 7/2006 | Steffensmeier et al. | |
| 2006/0195113 A1 | 8/2006 | Masini | |
| 2006/0244448 A1 | 11/2006 | Ballon et al. | |
| 2006/0271058 A1 | 11/2006 | Ashton et al. | |
| 2007/0010732 A1 | 1/2007 | DeYoe et al. | |
| 2007/0021838 A1 | 1/2007 | Dugas et al. | |
| 2007/0038059 A1 | 2/2007 | Sheffer et al. | |
| 2007/0055268 A1 | 3/2007 | Utz et al. | |
| 2007/0073305 A1 | 3/2007 | Lionberger et al. | |
| 2007/0083266 A1 | 4/2007 | Lang | |
| 2007/0100338 A1 | 5/2007 | Deffenbaugh et al. | |
| 2007/0100462 A1 | 5/2007 | Lang et al. | |
| 2007/0114370 A1 | 5/2007 | Smith et al. | |
| 2007/0118055 A1 | 5/2007 | McCombs | |
| 2007/0118243 A1 | 5/2007 | Schroeder et al. | |
| 2007/0123856 A1 | 5/2007 | Deffenbaugh et al. | |
| 2007/0123857 A1 | 5/2007 | Deffenbaugh et al. | |
| 2007/0123912 A1 | 5/2007 | Carson | |
| 2007/0162039 A1 | 7/2007 | Wozencroft | |
| 2007/0167833 A1 | 7/2007 | Redel et al. | |
| 2007/0173853 A1* | 7/2007 | MacMillan | A61B 17/1757 606/87 |
| 2007/0173858 A1 | 7/2007 | Engh et al. | |
| 2007/0191741 A1 | 8/2007 | Tsai et al. | |
| 2007/0213738 A1 | 9/2007 | Martin et al. | |
| 2007/0226986 A1 | 10/2007 | Park et al. | |
| 2007/0232959 A1 | 10/2007 | Couture et al. | |
| 2007/0233136 A1 | 10/2007 | Wozencroft | |
| 2007/0233141 A1 | 10/2007 | Park et al. | |
| 2007/0233269 A1 | 10/2007 | Steines et al. | |
| 2007/0237372 A1 | 10/2007 | Chen et al. | |
| 2007/0239167 A1* | 10/2007 | Pinczewski | A61B 17/154 606/87 |
| 2007/0249967 A1 | 10/2007 | Buly et al. | |
| 2007/0276224 A1 | 11/2007 | Lang et al. | |
| 2007/0276400 A1 | 11/2007 | Moore et al. | |
| 2008/0004701 A1 | 1/2008 | Axelson et al. | |
| 2008/0015599 A1 | 1/2008 | D'Alessio et al. | |
| 2008/0015600 A1 | 1/2008 | D'Alessio et al. | |
| 2008/0015602 A1 | 1/2008 | Axelson et al. | |
| 2008/0015606 A1 | 1/2008 | D'Alessio et al. | |
| 2008/0015607 A1 | 1/2008 | D'Alessio et al. | |
| 2008/0021299 A1 | 1/2008 | Meulink | |
| 2008/0033442 A1 | 2/2008 | Amiot et al. | |
| 2008/0058613 A1 | 3/2008 | Lang et al. | |
| 2008/0088761 A1 | 4/2008 | Lin et al. | |
| 2008/0089591 A1 | 4/2008 | Zhou et al. | |
| 2008/0114370 A1 | 5/2008 | Schoenefeld | |
| 2008/0153067 A1 | 6/2008 | Berckmans et al. | |
| 2008/0195108 A1 | 8/2008 | Bhatnagar et al. | |
| 2008/0234685 A1 | 9/2008 | Gjerde | |
| 2008/0257363 A1 | 10/2008 | Schoenefeld et al. | |
| 2008/0275452 A1 | 11/2008 | Lang et al. | |
| 2008/0287954 A1 | 11/2008 | Kunz et al. | |
| 2008/0312659 A1 | 12/2008 | Metzger et al. | |
| 2008/0319491 A1 | 12/2008 | Schoenefeld | |
| 2009/0024131 A1 | 1/2009 | Metzger et al. | |
| 2009/0085567 A1 | 4/2009 | Kimmlingen et al. | |
| 2009/0087276 A1 | 4/2009 | Rose | |
| 2009/0088674 A1 | 4/2009 | Caillouette et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1* | 4/2009 | Aram | A61B 17/155 606/87 |
| 2009/0088760 A1 | 4/2009 | Aaram et al. | |
| 2009/0088761 A1 | 4/2009 | Roose et al. | |
| 2009/0088763 A1 | 4/2009 | Aram et al. | |
| 2009/0089034 A1 | 4/2009 | Penney et al. | |
| 2009/0093816 A1 | 4/2009 | Roose et al. | |
| 2009/0112213 A1 | 4/2009 | Heavener et al. | |
| 2009/0125114 A1 | 5/2009 | May et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0151736 A1 | 6/2009 | Belcher et al. | |
| 2009/0163923 A1 | 6/2009 | Flett et al. | |
| 2009/0209884 A1 | 8/2009 | Van Vorhis et al. | |
| 2009/0222014 A1 | 9/2009 | Bojarski et al. | |
| 2009/0222015 A1 | 9/2009 | Park et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0248044 A1 | 10/2009 | Amiot et al. | |
| 2009/0254093 A1 | 10/2009 | White et al. | |
| 2009/0254367 A1 | 10/2009 | Belcher et al. | |
| 2009/0270868 A1 | 10/2009 | Park et al. | |
| 2009/0274350 A1 | 11/2009 | Pavlovskaia et al. | |
| 2009/0276045 A1 | 11/2009 | Lang | |
| 2009/0285465 A1 | 11/2009 | Haimerl et al. | |
| 2009/0306676 A1 | 12/2009 | Lang et al. | |
| 2009/0312805 A1 | 12/2009 | Lang et al. | |
| 2010/0016986 A1 | 1/2010 | Trabish | |
| 2010/0023015 A1 | 1/2010 | Park | |
| 2010/0042105 A1 | 2/2010 | Park et al. | |
| 2010/0082035 A1 | 4/2010 | Keefer | |
| 2010/0087829 A1 | 4/2010 | Metzger et al. | |
| 2010/0099977 A1 | 4/2010 | Hershberger | |
| 2010/0145344 A1 | 6/2010 | Jordan et al. | |
| 2010/0152741 A1 | 6/2010 | Park et al. | |
| 2010/0153076 A1 | 6/2010 | Bellettre et al. | |
| 2010/0153081 A1 | 6/2010 | Bellettre et al. | |
| 2010/0160917 A1 | 6/2010 | Fitz et al. | |
| 2010/0168754 A1 | 7/2010 | Fitz et al. | |
| 2010/0174376 A1 | 7/2010 | Lang | |
| 2010/0185202 A1 | 7/2010 | Lester et al. | |
| 2010/0191242 A1 | 7/2010 | Massoud | |

(56) References Cited

U.S. PATENT DOCUMENTS

| | | |
|---|---|---|
| 2010/0191244 A1 | 7/2010 | White et al. |
| 2010/0198351 A1 | 8/2010 | Meulink |
| 2010/0209868 A1 | 8/2010 | De Clerck |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0256479 A1 | 10/2010 | Park et al. |
| 2010/0262150 A1 | 10/2010 | Lian |
| 2010/0274253 A1 | 10/2010 | Ure |
| 2010/0274534 A1 | 10/2010 | Steines et al. |
| 2010/0292963 A1 | 11/2010 | Schroeder |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2010/0332194 A1 | 12/2010 | McGuan et al. |
| 2011/0016690 A1 | 1/2011 | Narainasamy et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0046735 A1 | 2/2011 | Metzger et al. |
| 2011/0054486 A1 | 3/2011 | Linder-Ganz et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092977 A1 | 4/2011 | Salehi et al. |
| 2011/0092978 A1 | 4/2011 | McCombs |
| 2011/0093108 A1 | 4/2011 | Ashby et al. |
| 2011/0106093 A1 | 5/2011 | Romano et al. |
| 2011/0112808 A1 | 5/2011 | Anderson et al. |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190899 A1 | 8/2011 | Pierce et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park |
| 2011/0218539 A1 | 9/2011 | Fitz et al. |
| 2011/0218542 A1 | 9/2011 | Lian |
| 2011/0218545 A1 | 9/2011 | Catanzarite et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0257653 A1 | 10/2011 | Hughes et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0295329 A1 | 12/2011 | Fitz et al. |
| 2011/0295378 A1 | 12/2011 | Bojarski et al. |
| 2011/0305379 A1 | 12/2011 | Mahfouz |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0004725 A1 | 1/2012 | Shterling et al. |
| 2012/0010711 A1 | 1/2012 | Antonyshyn et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0116203 A1 | 5/2012 | Vancraen et al. |
| 2012/0123420 A1 | 5/2012 | Honiball |
| 2012/0130382 A1 | 5/2012 | Lannotti et al. |
| 2012/0130434 A1 | 5/2012 | Stemniski |
| 2012/0143197 A1 | 6/2012 | Lang et al. |
| 2012/0143198 A1 | 6/2012 | Boyer et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165820 A1 | 6/2012 | De Smedt et al. |
| 2012/0165821 A1 | 6/2012 | Carignan et al. |
| 2012/0172882 A1 | 7/2012 | Sato |
| 2012/0179147 A1 | 7/2012 | Geebelen et al. |
| 2012/0191205 A1 | 7/2012 | Bojarski et al. |
| 2012/0191420 A1 | 7/2012 | Bojarski et al. |
| 2012/0197260 A1 | 8/2012 | Fitz et al. |
| 2012/0197408 A1 | 8/2012 | Lang et al. |
| 2012/0203233 A1 | 8/2012 | Yoshida et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0230566 A1 | 9/2012 | Dean et al. |
| 2012/0230573 A1 | 9/2012 | Ito et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0239045 A1 | 9/2012 | Li |
| 2012/0265496 A1 | 10/2012 | Mahfouz |
| 2012/0265499 A1 | 10/2012 | Mahfouz et al. |
| 2012/0310400 A1 | 12/2012 | Park |
| 2013/0115474 A1 | 5/2013 | Park |
| 2013/0116697 A1 | 5/2013 | Park et al. |
| 2013/0123789 A1 | 5/2013 | Park |
| 2013/0190767 A1 | 7/2013 | Park et al. |
| 2013/0197526 A1 | 8/2013 | Park et al. |
| 2013/0197687 A1 | 8/2013 | Pavlovskaia et al. |
| 2014/0005997 A1 | 1/2014 | Park |
| 2014/0078139 A1 | 3/2014 | Park et al. |
| 2014/0081277 A1 | 3/2014 | Park et al. |
| 2014/0128875 A1 | 5/2014 | Park et al. |
| 2014/0276872 A1 | 9/2014 | Song |
| 2014/0324205 A1 | 10/2014 | Park et al. |
| 2014/0330278 A1 | 11/2014 | Park et al. |
| 2014/0330279 A1 | 11/2014 | Park et al. |
| 2014/0378978 A1 | 12/2014 | Park |

FOREIGN PATENT DOCUMENTS

| | | |
|---|---|---|
| EP | 0097001 A | 12/1983 |
| EP | 0574098 A | 12/1993 |
| EP | 0622052 A | 11/1994 |
| EP | 0709061 A1 | 5/1996 |
| EP | 0908836 A2 | 4/1999 |
| EP | 0908836 A3 | 12/1999 |
| EP | 1059153 A2 | 12/2000 |

(56) References Cited

FOREIGN PATENT DOCUMENTS

| | | |
|---|---|---|
| EP | 1486900 A1 | 12/2004 |
| EP | 1532939 A1 | 5/2005 |
| EP | 1669033 A1 | 6/2006 |
| FR | 2478462 A1 | 9/1981 |
| GB | 2215610 A1 | 9/1989 |
| GB | 2420717 A | 6/2006 |
| GB | 2447702 A | 9/2008 |
| JP | 10-94538 | 4/1998 |
| JP | 2001-092950 | 4/2001 |
| JP | P 2005-287813 | 10/2005 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 98/32384 | 7/1998 |
| WO | WO 00/35346 | 6/2000 |
| WO | WO 01/00096 A1 | 1/2001 |
| WO | WO 01/70142 A1 | 9/2001 |
| WO | WO 01/85040 A1 | 11/2001 |
| WO | WO 02/96268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/127486 A2 | 11/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |
| WO | WO 2007/097853 A2 | 8/2007 |
| WO | WO 2007/097854 A2 | 8/2007 |
| WO | WO 2007/137327 A1 | 12/2007 |
| WO | WO 2008/014618 A1 | 2/2008 |
| WO | WO 2008/091358 A1 | 7/2008 |
| WO | WO 2011/106409 A1 | 9/2011 |
| WO | WO 2012/051542 A2 | 4/2012 |

OTHER PUBLICATIONS

U.S. Appl. No. 14/335,431, filed Jul. 18, 2014, Park et al.
U.S. Appl. No. 14/335,460, filed Jul. 18, 2014, Park et al.
U.S. Appl. No. 13/923,093, filed Jun. 20, 2013, Park.
U.S. Appl. No. 13/960,498, filed Aug. 6, 2013, Song.
U.S. Appl. No. 14/011,998, filed Aug. 28, 2013, Park et al.
U.S. Appl. No. 14/084,255, filed Nov. 19, 2013, Park et al.
U.S. Appl. No. 14/086,849, filed Nov. 21, 2013, Park et al.
U.S. Appl. No. 14/086,878, filed Nov. 21, 2013, Park et al.
Advisory Action, U.S. Appl. No. 11/642,385, dated Aug. 1, 2014.
Amendment and Response After Final Office Action, U.S. Appl. No. 11/656,323, dated Aug. 25, 2014.
Appeal Brief, U.S. Appl. No. 11/642,385, dated Oct. 7, 2014.
Canadian Office Action, Appl. No. 2708393, dated Jul. 29, 2014.
European Search Report, EP09823986.6, dated Sep. 23, 2014.
Final Office Action, U.S. Appl. No. 11/946,002, dated Sep. 17, 2014.
International Search Report and Written Opinion, PCT/US2014/030496, dated Aug. 6, 2014.
Non-Final Office Action, U.S. Appl. No. 11/656,323, dated Sep. 18, 2014.
Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
Delp et al. "An Interactive Graphics-Based Model of the lower Extremity to Study Orthopaedic Surgical Procedures." *IEEE Transactions on Biomedical Engineering*, vol. 37, No. 8, Aug. 1990.
Garg, A. et al . . . "Prediction of Total Knee Motion Using a Three-Dimensional Computer-Graphics Model." *J. Biomechanics*, vol. 23, No. 1, pp. 45-58, 1990.

Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.
Walker, P. S. et al. "Range of Motion in Total Knee Arthroplasty: A Computer Analysis." *Clinical Orthopaedics and Related Research*, No. 262, Jan. 1991.
European Search Report, EP 09835583.7, dated May 9, 2014.
European search Report, European Appl. No. 08863202.1, dated May 16, 2014.
Extended European search Report, European Appl. No. 13188389.4, dated Jan. 8, 2014.
Final Office Action, U.S. Appl. No. 11/642,385, dated Apr. 25, 2014.
Final Office Action, U.S. Appl. No. 11/656,323, dated Apr. 3, 2014.
Final Office Action, U.S. Appl. No. 12/505,056, dated Dec. 30, 2013, 48 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Japanese Office Action, JP Application No. 2011-507530, dated Dec. 17, 2013, 8 pages.
Non-Final Office Action, U.S. Appl. No. 11/946,002, dated Feb. 6, 2014, 46 pages.
Non-Final Office Action, U.S. Appl. No. 13/488,505, dated Jul. 17, 2014.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/760,388, dated Jan. 22, 2014, 13 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014.
Preliminary Amendment, U.S. Appl. No. 13/731,850, filed Apr. 11, 2014, 8 pages.
Response to Final Office Action, U.S. Appl. No. 11/641,569, dated Jan. 29, 2014, 10 pages.
Response to Final Office Action, U.S. Appl. No. 11/642,385, dated Jul. 22, 2014.
Response to Final Office Action, U.S. Appl. No. 12/390,667, dated Dec. 23, 2013, 5 pages.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Non-Final Office Action, U.S. Appl. No. 11/946,002, dated Jul. 7, 2014.
Response to Restriction, U.S. Appl. No. 13/488,505, dated May 5, 2014, 7 pages.

(56) References Cited

OTHER PUBLICATIONS

Restriction Requirement, U.S. Appl. No. 13/488,505, dated Mar. 4, 2014, 5 pages.
Siemens Magnetom Sonata 1.5T Technical Specifications, pp. 1-4, accessed online Jan. 28, 2014.
Supplementary European Search Report and Opinion, EP 09739474.6, dated Feb. 27, 2014, 7 pages.
U.S. Appl. No. 14/476,500, filed Sep. 3, 2014, Park.
Advisory Action and Interview Summary, U.S. Appl. No. 12/390,667, mailed Apr. 27, 2012, 23 pages.
Advisory Action, U.S. Appl. No. 11/642,385, dated Oct. 29, 2010, 3 pages.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action and Petition to Revive, U.S. Appl. No. 10/146,862, filed Jan. 18, 2006, 29 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
Amendment Under 37 C.F.R. 1.312, U.S. Appl. No. 12/386,105, filed Oct. 1, 2012, 6 pages.
Amendment Under 37 C.F.R. 1.312, U.S. Appl. No. 13/374,960, filed May 7, 2013, 6 pages.
Appeal Brief, U.S. Appl. No. 12/390,667, filed Jul. 12, 2012, 32 pages.
Appeal Brief, U.S. Appl. No. 12/391,008, filed Oct. 16, 2012, 24 pages.
European Search Report, 10192631.9-2310, dated Mar. 17, 2011, 5 pages.
European Search Report, EP09739422.5, dated Mar. 28, 2013, 9 pages.
Ex Parte Quayle Action, U.S. Appl. No. 29/296,687, mailed Jan. 24, 2011, 11 pages.
Examiner's Answer in appeal, U.S. Appl. No. 12/391,008, mailed Dec. 13, 2012, 27 pages.
Final Office Action and PTO-892, U.S. Appl. No. 11/641,382, mailed Aug. 5, 2010, 13 pages.
Final Office Action and PTO-892, U.S. Appl. No. 11/656,323, mailed Sep. 3, 2010, 11 pages.
Final Office Action, U.S. Appl. No. 11/641,569, mailed May 10, 2010, 9 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Final Office Action, U.S. Appl. No. 11/641,382, mailed Jul. 25, 2012, 12 pages.
Final Office Action, U.S. Appl. No. 11/641,569, dated Nov. 29, 2013, 20 pages.
Final Office Action, U.S. Appl. No. 11/641,569, mailed Mar. 1, 2012, 12 pages.
Final Office Action, U.S. Appl. No. 11/924,425, mailed Jul. 6, 2012, 14 pages.
Final Office Action, U.S. Appl. No. 11/946,002, mailed May 9, 2012, 24 pages.
Final Office Action, U.S. Appl. No. 12/390,667, dated Oct. 25, 2013, 17 pages.
Final Office Action, U.S. Appl. No. 12/391,008, mailed May 17, 2012, 28 pages.
Final Office Action, U.S. Appl. No. 12/546,545, dated Oct. 7, 2013, 24 pages.
Final Office Action, U.S. Appl. No. 12/563,809, dated Mar. 7, 2013, 14 pages.
International Search Report and Written Opinion, International Application No. PCT/US2009/034983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
International Search Report and Written Opinion, International Application No. PCT/US2009/040629, mailed Aug. 6, 2009, 9 pages.
International Search Report and Written Opinion, International Application No. PCT/US2009/051109, mailed Nov. 6, 2009, 13 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2007/001624, dated Dec. 12, 2007, 14 pages.
International Search Report and Written Opinion, PCT/US2007/001622, dated Jun. 11, 2007, 14 pages.
International Search Report and Written Opinion, PCT/US2008/083125, dated Mar. 9, 2009, 13 pages.
International Search Report and Written Opinion, PCT/US2011/032342, dated Jul. 1, 2011, 8 pages.
Non-Final Office Action and PTO-892, U.S. Appl. No. 11/641,382, mailed Jan. 20, 2010, 12 pages.
NonFinal Office Action and PTO-892, U.S. Appl. No. 11/642,385, mailed Mar. 2, 2010, 11 pages.
Non-Final Office Action and PTO-892, U.S. Appl. No. 11/656,323, mailed Mar. 30, 2010, 10 pages.
Non-Final Office Action, U.S. Appl. No. 11/641,569, dated Aug. 3, 2011, 14 pages.
Non-Final Office Action, U.S. Appl. No. 11/641,569, dated Jan. 3, 2013, 12 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 13/086,275, mailed Feb. 7, 2013, 36 pages.
Non-Final Office Action, U.S. Appl. No. 11/641,382, mailed Mar. 29, 2012, 24 pages.
Non-Final Office Action, U.S. Appl. No. 11/641,569, mailed Jul. 12, 2013, 21 pages.
NonFinal Office Action, U.S. Appl. No. 11/641,569, mailed Nov. 12, 2009, 9 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/946,002, dated Nov. 25, 2011, 44 pages.
Non-Final Office Action, U.S. Appl. No. 11/946,002, dated Oct. 2, 2013, 39 pages.

(56) References Cited

OTHER PUBLICATIONS

Nonfinal Office Action, U.S. Appl. No. 11/959,344, dated Feb. 15, 2011, 29 pages.
Non-Final Office Action, U.S. Appl. No. 12/111,924, mailed Jun. 29, 2012, 35 pages.
Non-Final Office Action, U.S. Appl. No. 12/386,105, dated Feb. 9, 2012, 30 pages.
Non-Final Office Action, U.S. Appl. No. 12/390,667, mailed Sep. 26, 2012, 21 pages.
Non-Final Office Action, U.S. Appl. No. 12/390,667, mailed May 8, 2013, 20 pages.
Non-Final Office Action, U.S. Appl. No. 12/391,008, mailed Oct. 31, 2011, 44 pages.
Non-Final Office Action, U.S. Appl. No. 12/505,056, mailed Jun. 28, 2013, 7 pages.
Non-Final Office Action, U.S. Appl. No. 12/546,545, mailed Jul. 19, 2012, 28 pages.
Non-Final Office Action, U.S. Appl. No. 12/546,545, mailed Mar. 13, 2013, 10 pages.
Non-Final Office Action, U.S. Appl. No. 12/563,809, mailed Sep. 21, 2012, 32 pages.
Non-Final Office Action, U.S. Appl. No. 12/636,939, mailed Jul. 20, 2012, 25 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/374,960, mailed Aug. 1, 2012, 6 pages.
Non-Final Office Action, U.S. Appl. No. 13/723,904, mailed Aug. 9, 2013, 6 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 13/066,568, mailed Oct. 26, 2011, 28 pages.
Notice of Allowance, U.S. Appl. No. 29/394,882, mailed Feb. 4, 2013, 32 pages.
Notice of Allowance, U.S. Appl. No. 29/394,882, mailed May 24, 2013, 16 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.
Notice of Allowance, U.S. Appl. No. 11/959,344, mailed Mar. 5, 2012, 13 pages.
Notice of Allowance, U.S. Appl. No. 12/111,924, mailed Mar. 11, 2013, 14 pages.
Notice of Allowance, U.S. Appl. No. 12/386,105, mailed Jul. 5, 2012, 11 pages.
Notice of Allowance, U.S. Appl. No. 12/563,809, mailed May 28, 2013, 11 pages.
Notice of Allowance, U.S. Appl. No. 12/636,939, dated Oct. 7, 2013, 28 pages.
Notice of Allowance, U.S. Appl. No. 13/086,275, mailed Aug. 27, 2013, 31 pages.
Notice of Allowance, U.S. Appl. No. 13/374,960, mailed Nov. 2, 2012, 24 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Notice of Allowance, U.S. Appl. No. 29,296,687, mailed Mar. 31, 2011, 18 pages.
Notice of Non-Compliant Amendment, U.S. Appl. No. 11/641,569, mailed Aug. 7, 2009, 3 pages.
Office Action (Restriction Requirement), U.S. Appl. No. 12/563,809, dated Feb. 2, 2012, 7 pages.
Office Action, U.S. Appl. No. 10/146,862, mailed Jan. 13, 2005, 10 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
Preliminary Amendment, U.S. Appl. No. 13/731,697, filed May 10, 2013, 6 pages.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
RCE/Amendment, U.S. Appl. No. 11/946,002, filed Sep. 6, 2012, 38 pages.
Response to Final Office Action, U.S. Appl. No. 12/546,545, filed Feb. 20, 2013, 13 pages.
Response to Final Office Action, U.S. Appl. No. 11/641,569, filed Jun. 28, 2012, 10 pages.
Response to Final Office Action, U.S. Appl. No. 11/641,382, filed Sep. 24, 2012, 11 pages.
Response to Final Office Action, U.S. Appl. No. 11/959,344, filed Dec. 27, 2011, 16 pages.
Response to Final Office Action, U.S. Appl. No. 11/924,425, filed Sep. 5, 2012, 9 pages.
Response to Final Office Action, U.S. Appl. No. 12/390,667, filed Mar. 12, 2012, 19 pages.
Response to Final Office Action, U.S. Appl. No. 12/563,809, filed May 6, 2013, 15 pages.
Response to Final Office Action, U.S. Appl. No. 12/546,545, dated Dec. 9, 2013, 8 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 12/563,809, filed Dec. 13, 2012, 15 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.

(56) References Cited

OTHER PUBLICATIONS

Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Response to Restriction Requirement, U.S. Appl. No. 12/391,008, filed Aug. 29, 2011, 9 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction Requirement, U.S. Appl. No. 12/760,388, filed Apr. 5, 2013, 7 pages.
Response to Restriction, U.S. Appl. No. 12/563,809, filed Aug. 6, 2012, 10 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
Restriction Requirement, U.S. Appl. No. 11/641,382, mailed Sep. 3, 2009, 6 pages.
Restriction Requirement, U.S. Appl. No. 11/641,569, mailed Apr. 27, 2009, 7 pages.
Restriction Requirement, U.S. Appl. No. 11/642,385, mailed Oct. 27, 2009, 7 pages.
Restriction Requirement, U.S. Appl. No. 11/656,323, mailed Nov. 13, 2009, 10 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 11/959,344, dated Oct. 29, 2010, 6 pages.
Restriction Requirement, U.S. Appl. No. 12/111,924, mailed Mar. 19, 2012, 8 pages.
Restriction Requirement, U.S. Appl. No. 12/386,105, dated Oct. 24, 2011, 7 pages.
Restriction Requirement, U.S. Appl. No. 12/390,667, dated Jul. 14, 2011, 9 pages.
Restriction Requirement, U.S. Appl. No. 12/391,008, dated Aug. 18, 2011, 6 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
Restriction Requirement, U.S. Appl. No. 12/760,388, mailed Mar. 6, 2013, 7 pages.
Restriction Requirement, U.S. Appl. No. 29/296,687, mailed Sep. 21, 2010, 7 pages.
Akca, "Matching of 3D Surfaces and Their Intensities," ISPRS Journal of Photogrammetry & Remote Sensing, 62(2007), 112-121.
Akenine-Möller et al., *Real-Time Rendering, Second Edition*, AK Peters, Natick, MA, 6 pages (Table of Contents), 2002.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Audette et al. "An algorithmic overview of surface registration techniques for medical imaging." Medical Image Analysis, vol. 4, No. 3, Sep. 1, 2000, pp. 201-217.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," *Computer Aided Geometric Design*, vol. 12, pp. 207-229, 1995.
Barequet et al., "Repairing CAD Models," Proceedings of the 8th IEEE Visualization '97 Conference, pp. 363-370, Oct. 1997.
Bargar et al., "Robotic Systems in Surgery," Orthopedic and Spine Surgery, Surgical Technology International II, 1993, 419-423.
Berry et al., "Personalised image-based templates for intra-operative guidance," *Proc. Inst. Mech. Eng. Part H: J. Engineering in Medicine*, vol. 219, pp. 111-118, Oct. 7, 2004.
Besl et al., "A Method for Registration of 3-D Shapes," IEEE Transactions on Pattern Analysis and Machine Intelligence (PAMI), 14(2):239-256, Feb. 1992.
Biščević et al., "Variations of Femoral Condyle Shape," *Coll. Antropol.*, vol. 29 No. 2, pp. 409-414, 2005.
Blaha et al., "Using the Transepicondylar Axis to Define the Sagittal Morphology of the Distal Part of the Femur," J Bone Joint Surg Am. 2002;84-A Suppl 2:48-55.
Blinn, *Jim Blinn's Corner—A Trip Down the Graphics Pipeline*, Morgan Kaufmann Publishers, Inc., San Francisco, CA, 5 pages (Table of Contents), 1996.
Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.

(56) References Cited

OTHER PUBLICATIONS

Canny, "A computational Approach to Edge Detection," IEEE Transactions on Pattern Analysis and Machine Intelligence, PAMI 8(6), pp. 679-698 (1986).
Chauhan et al., "Computer-assisted knee arthroplasty *versus* a conventional jig-based technique—a randomised, prospective trial," *The Journal of Bone and Joint Surgery*, vol. 86-B, No. 3, pp. 372-377, Apr. 2004.
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Cohen et al., *Radiosity and Realistic Image Synthesis*, Academic Press Professional, Cambridge, MA, 8 pages (Table of Contents), 1993.
Couglin et al., "Tibial Axis and Patellar Position Relative to the Femoral Epicondylar Axis During Squatting," *The Journal of Arthroplasty*, vol. 18, No. 8, Elsevier, 2003.
Delp et al., "Computer Assisted Knee Replacement," *Clinical Orthopaedics and Related Research*, No. 354, pp. 49-56, Sep. 1998.
Dutré et al., *Advanced Global Illumination*, AK Peters, Natick, MA, 5 pages (Table of Contents), 2003.
Eckhoff et al., "Difference Between the Epicondylar and Cylindrical Axis of the Knee," Clin Orthop Relat Res. 2007;461:238-44.
Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clin orthop Relat Res. 1990(260):98-103.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., *Landscape Modeling*, McGraw-Hill, New York, NY, 8 pages (Table of Contents), 2001.
Farin, *NURB Curves and Surfaces: From Projective Geometry to Practical Use*, AK Peters, Wellesley, MA, 7 pages (Table of Contents), 1995.
Favorito et al., "total Knee Arthroplasty in the Valgus Knee," Journal Am Acad Orthop surg. 2002;10(1):16-24.
Fleischer et al., "Accurate Polygon Scan Conversion Using Half-Open Intervals," *Graphics Gems III*, pp. 362-365, code: pp. 599-605, 1992.
Foley et al., *Computer Graphics: Principles and Practice*, Addison-Wesley Publishing Company, Reading, MA, 9 pages (Table of Contents), 1990.
Freeman et al., "The Movement of the Knee Studied by Magnetic Resonance Imaging," Clinical orthop Relat Res. 2003 (410):35-43.
Freeman et al., "The Movement of the Normal Tibio-Femoral Joint," Journal Biomech. 2005;38(2):197-208.
Glassner (editor), *An Introduction to Ray Tracing*, Academic Press Limited, San Diego, CA, 4 pages (Table of Contents), 1989.
Glassner, *Principles of Digital Image Synthesis*, vols. One and Two, Morgan Kaufmann Publishers, Inc., San Francisco, CA, 32 pages (Table of Contents), 1995.
Gooch et al., *Non-Photorealistic Rendering*, AK Peters, Natick, MA, 4 pages (Table of Contents), 2001.
Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "Least Squares 3D Surface and Curve Matching," ISPRS Journal of Photogrammetry & Remote Sensing, 59(2005), 151-174.
Grüne et al., "On numerical algorithm and interactive visualization for optimal control problems," *Journal of Computation and Visualization in Science*, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Hafez et al., "Computer Assisted Total Knee Replacement: Could a Two-Piece Custom Template Replace the Complex Conventional Instrumentations?", *Computer Aided Surgery*, vol. 9, No. 3, pp. 93-94, 2004.
Hafez et al., "Computer-Assisted Total Knee Arthroplasty Using Patient-Specific Templating," *Clinical Orthopaedics and Related Research*, No. 0, pp. 1-9, 2006.
Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: FACT and FICTION Syllabus, San Diego, CA, 8 pages, Oct. 20-22, 2005.
Hollister et al., "The Axes of Rotation of the Knee," Clin Orthop Relat Res. 1993(290):259-68.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Ibáñez et al., The ITK Software Guide, Second Edition, Updated for ITK version 2.4, Nov. 21, 2005, pp. 114, 396-411, and 426.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Jensen, *Realistic Image Synthesis Using Photon Mapping*, AK Peters, Natick, MA, 7 pages (Table of Contents), 2001.
Johnson, "Joint Remodeling as the Basis for Osteoarthritis," Journal Am Vet Med Assoc. 1962, 141:1233-41.
Jones et al., "A new approach to the construction of surfaces from contour data," *Computer Graphics Forum*, vol. 13, No. 3, pp. 75-84, 1994 [ISSN 0167-7055].
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Khorramabadi, "A Walk Through the Planned CS Building," Technical Report UCB/CSD 91/652, Computer Science Department, University of California at Berkeley, 74 pages, 1991.
Kidder et al., "3-D Model Acquisition, Design, Planning and Manufacturing of Orthopaedic Devices: A Framework," *Advanced Sensor and Control-System Interface* (B.O. Nnaji editor), Proceedings SPIE—The International Society for Optical Engineering, Bellingham, WA, vol. 2911, pp. 9-22, Nov. 21-22, 1996.
Kienzel III et al., "An Integrated CAD-Robotics System for Total Knee Replacement Surgery", IEEE International Conference, pp. 889-894, vol. 1, May 1993.
Kienzel III et al., "Total Knee Replacement," IEEE May/Jun. 1995.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.

(56) References Cited

OTHER PUBLICATIONS

Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.
Kunz et al., "Computer Assisted Hip Resurfacing Using Individualized Drill Templates," *The Journal of Arthroplasty*, vol. 00, No. 0, pp. 1-7, 2009.
Kusumoto et al., "Application of Virtual Reality Force Feedback Haptic Device for Oral Implant Surgery", Graduate School of Dentistry Course for Integrated Oral Science and Stomatology, Jun. 16, 2005.
Lea et al., "Registration and immobilization in robot-assisted surgery", Journal of Image Guided Surgery, pp. 1-10, 1995.
Lorensen et al., "Marching Cubes: A High Resolution 3d Surface Construction Algorithm," *Computer Graphics*, vol. 21, No. 4, pp. 163-169, 1987.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using A 2d/3d Database", Dept. of Surgery, Trauma Unit, University Hospital, Bassel, Switzerland, *Computer Aided Surgery* 6:183-194 (2001).
Mihalko et al., "The Variability of Intramedullary Alignment of the Femoral Component During Total Knee Arthroplasty," Journal Arthroplasty. 2005;20(1):25-8.
Mole et al., "A New Three-Dimensional Treatment Algorithm for Complex Surfaces: Applications in Surgery", Feb. 1995.
Morvan et al., IVECS, Interactively Correcting .STL Files in a Virtual Environment, Clemson University, Clemson, SC, Proc. Conf. Virtual Design, Aug. 1996.
Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Platt et al., "Mould Arthroplasty of the Knee, A Ten-Year Follow-up Study," *The Journal of Bone and Joint Surgery* (British Volume), vol. 51-B, No. 1, pp. 76-87, Feb. 1969.
Potter, "Arthroplasty of the Knee with Tibial Metallic Implants of the McKeever and MacIntosh Design," *The Surgical Clinics of North America*, vol. 49, No. 4, pp. 903-915, Aug. 1969.
Radermacher et al., "Computer Assisted Orthopaedic Surgery with Image Based Individual Templates," *Clinical Orthopaedics and Related Research*, vol. 354, pp. 28-38, Sep. 1998.
Rohlfing et al., "Chapter 11 *Quo Vadis*, Atlas-Based Segmentation?", in Handbook of Biomedical Image Analysis vol. III: Registration Models 435, 435-486 (Jasjit S. Suri et al. eds., Kluwer Academic/Plenum Publishers, NY 2005).
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Shirley et al., *Realistic Ray Tracing, Second Edition*, AK Peters, Natick, MA, 7 pages (Table of Contents), 2003.
Siston et al., "Averaging Different Alignment Axes Improves Femoral Rotational Alignment in Computer-Navigated Total Knee Arthroplasty," Journal Bone Joint Surg Am. 2008;90(10):2098-104.
Siston et al., "The Variability of Femoral Rotational Alignment in Total Knee Arthroplasty," Journal Bone Joint Surg Am. 2005;87(10):2276-80.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Strothotte et al., *Non-Photorealistic Computer Graphics—Modeling, Rendering, and Animation*, Morgan Kaufmann Publishers, San Francisco, CA, 9 pages (Table of Contents), 2002.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Vande Berg et al., "Assessment of Knee Cartilage in Cadavers with Dual-Detector Spiral CT Arthrography and MR Imaging," *Radiology*, vol. 222, No. 2, pp. 430-436, Feb. 2002.
Wikipedia, the Free Encyclopedia, "CNC," (date unknown) located at http://en.wikipedia.org/wiki/CNC>, 6 pages, last visited on Apr. 12, 2007.
Wright Medical Technology, Inc., "Prophecy Pre-Operative Navigation Guides Surgical Technique," 2009.
Xie et al. "Segmentation by surface-to-image registration." proceedings of SPIE, vol. 6144, Mar. 2, 2006, pp. 614405-1-614405-7.
Australian Patent Examination Report No. 1, AU 2013200861, dated Mar. 3, 2015.
Non-Final Office Action, U.S. Appl. No. 13/731,697, dated Jan. 29, 2015.
Notice of Allowance, U.S. Appl. No. 11/656,323, dated Feb. 3, 2015.
Reply Brief, U.S. Appl. No. 11/642,385, dated Jan. 23, 2015.
Response to Restriction, U.S. Appl. No. 14/476,500, dated Mar. 17, 2015.
Restriction Requirement, U.S. Appl. No. 14/476,500, dated Feb. 25, 2015.
Canadian Office Action, CA2721762, dated Nov. 10, 2015.
Decision on Appeal, U.S. Appl. No. 12/391,008, dated Dec. 11, 2015.
Final Office Action, U.S. Appl. No. 11/946,002, dated Nov. 30, 2015.
Non-Final Office Action, U.S. Appl. No. 13/923,093, dated Dec. 2, 2015.
Calvo et al., "High Resolution MRI Detects Cartilage Swelling at the Early Stages of Experimental Osteoarthritis," OARSI, 2001, pp. 463-472.
Canadian Office Action, Appl. No. 2642616, dated Apr. 22, 2015.
Canadian Office Action, CA2708393, dated May 7, 2015.
Canadian Office Action, CA2721735, dated Jul. 7, 2015.
European Examination Report, EP10192631.9, dated Feb. 11, 2015.
European Patent Office, Summons to Attend Oral Proceedings, EP07749030.8, dated Sep. 10, 2015.

(56) References Cited

OTHER PUBLICATIONS

European Search Report, EP09718014.5, dated May 13, 2015.
European Search Report, EP09718041.8, dated May 12, 2015.
Japanese Office Action, JP2014-147908, dated Jun. 9, 2015.
Non-Final Office Action, U.S. Appl. No. 11/946,002, dated Jun. 29, 2015.
Non-Final Office Action, U.S. Appl. No. 14/476,500, dated Jun. 18, 2015.
Notice of Allowance, U.S. Appl. No. 13/731,697, dated Jul. 29, 2015.
Notice of Allowance, U.S. Appl. No. 14/824,731, dated Oct. 20, 2015.
Response to Non-Final Office Action, U.S. Appl. No. 13/731,697, dated May 26, 2015.
Response to Non-Final Office Action, U.S. Appl. No. 11/946,002, dated Sep. 29, 2015.
Response to Non-Final Office Action, U.S. Appl. No. 14/476,500, dated Oct. 16, 2015.
Restriction Requirement, U.S. Appl. No. 13/960,498, dated Sep. 23, 2015.

* cited by examiner

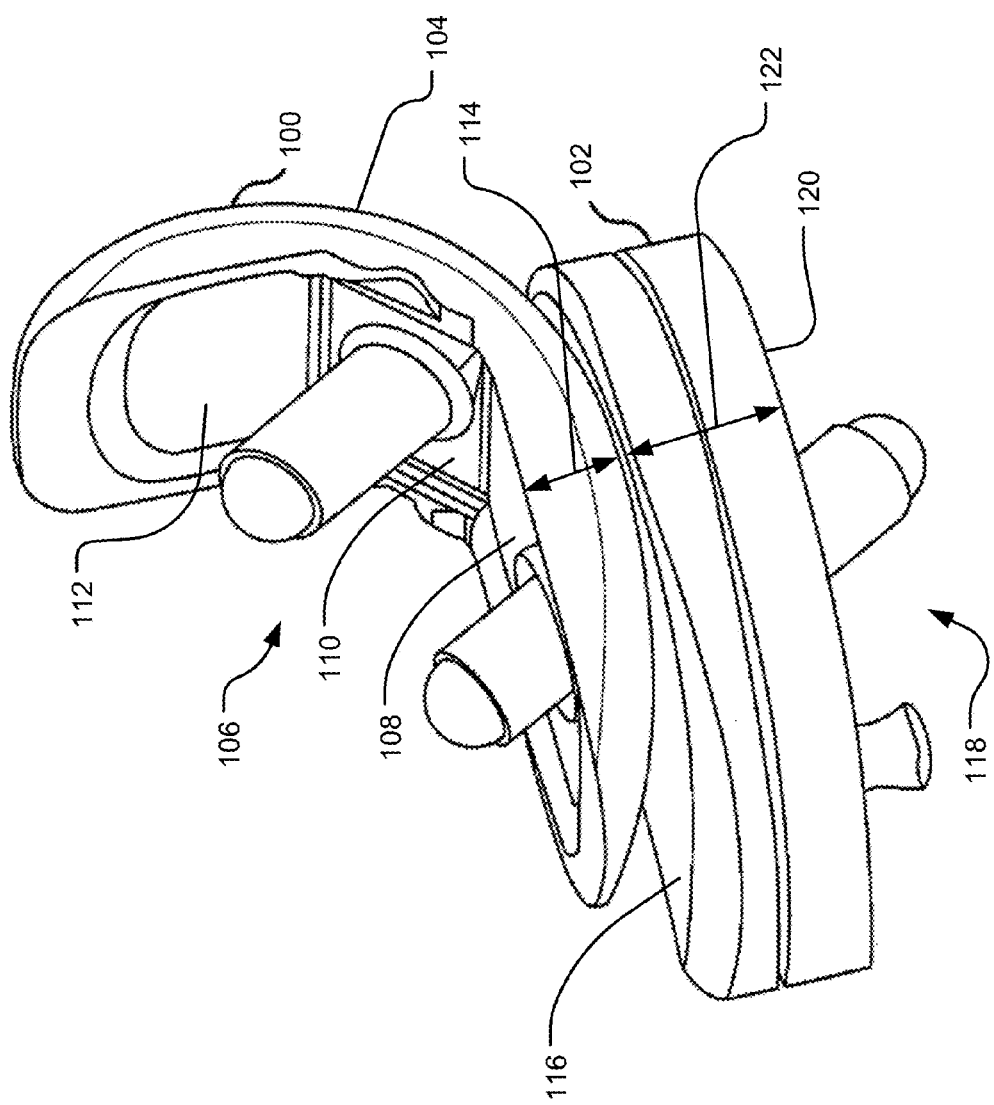

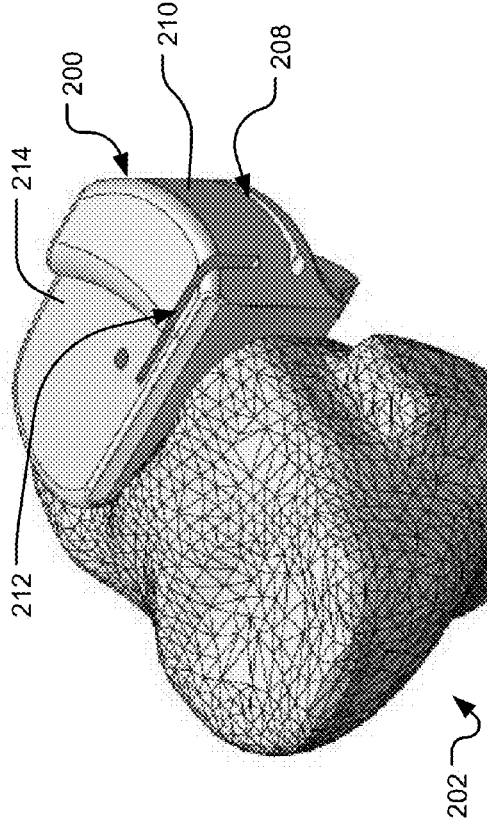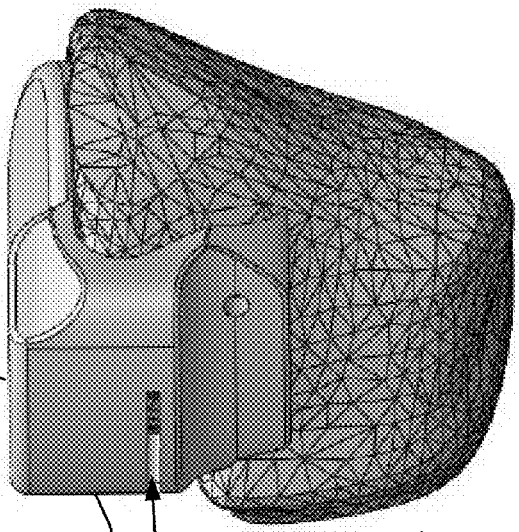
FIG. 2B
FIG. 2C

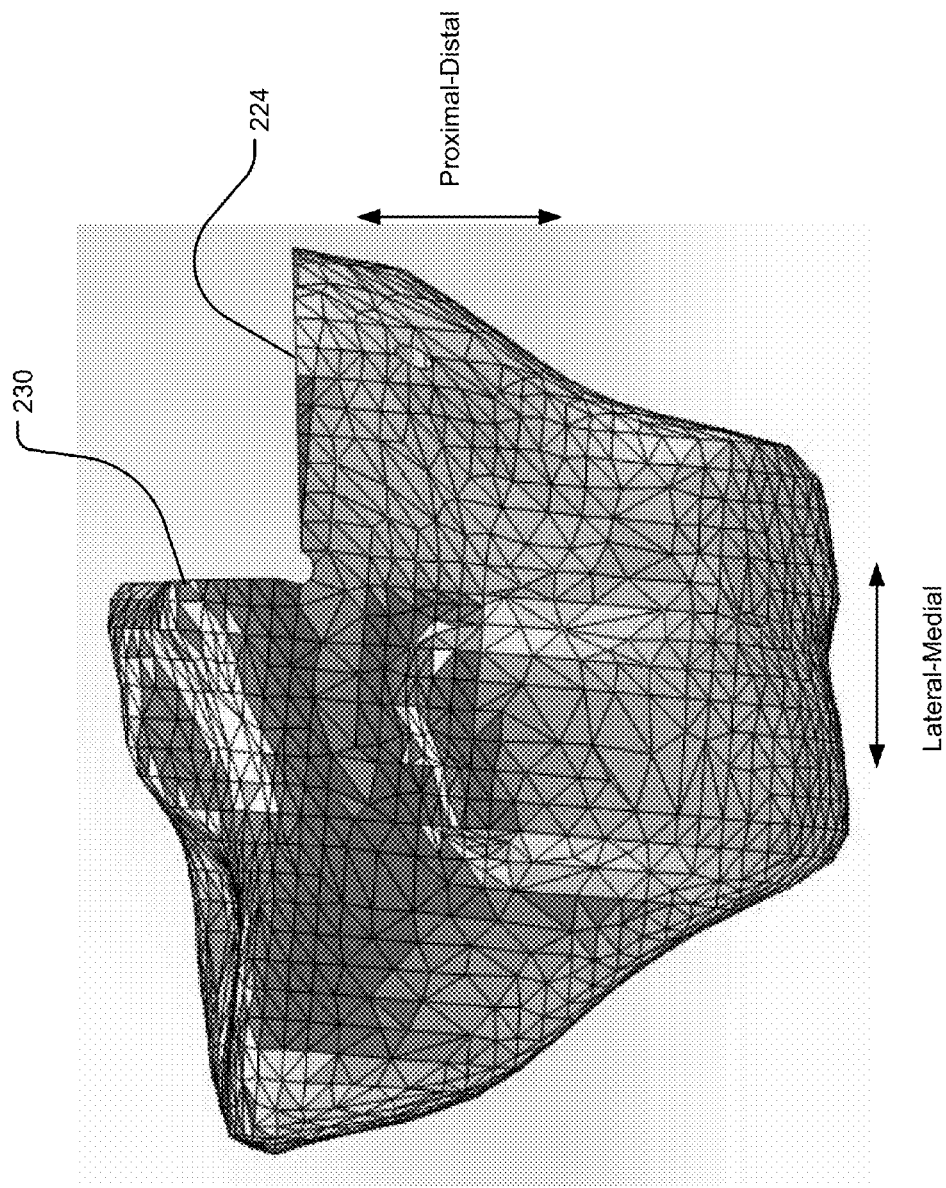

CUSTOMIZED ARTHROPLASTY CUTTING GUIDES AND SURGICAL METHODS USING THE SAME

CROSS REFERENCE TO RELATED APPLICATIONS

The present application claims priority under 35 U.S.C. §119 to U.S. provisional patent application 61/712,577, which was filed Oct. 11, 2012, entitled "PKR Cutting Guide," and is hereby incorporated by reference in its entirety into the present application.

FIELD OF THE INVENTION

Aspects of the presently disclosed technology relate to medical apparatuses and methods. More specifically, the presently disclosed technology relates to unicompartmental customized arthroplasty cutting guides and surgical methods using such cutting guides.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. Typically, a candidate for a TKA has significant wear or damage in tow or more "compartments" of the knee. The knee is generally divided into three "compartments, including: medial (the inside part of the knee), lateral (the outside part of the knee), and the patellofemoral (the joint between the knee cap and the thighbone). During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Another type of arthroplasty procedure is a unicompartmental (knee) arthroplasty or a partial knee replacement ("UKA") in which only a portion (or a single compartment) of the knee is removed and replaced with prosthetic implants. Typically, a candidate for a UKA has significant wear or damage confined to primarily one compartment of the knee. A UKA may be a less invasive approach than a TKA and may have a quicker recovery time. A UKA may be utilized to prevent the spread of disease, such as in the early stages of osteoarthritis where the disease has only affected a portion of the knee and it is desirable to prevent the disease from spreading to other portions of the knee.

Implants that are implanted into a damaged region may provide support and structure to the damaged region and may help to restore the damaged region, thereby enhancing its functionality. Prior to implantation of an implant in a damaged region, the damaged region is prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA or UKA procedure. A one to two millimeter translational misalignment may result in imbalanced ligaments and thus may significantly affect the outcome of the procedure. For example, implant misalignment may result in intolerable post-surgery pain and also may prevent the patient from having full leg extension and stable leg flexion.

To achieve accurate implant alignment, prior to treating (e.g., cut, drilled, reamed, and/or resurfaced) any regions of a bone, it is important to correctly determine the location at which the treatment will take place and how the treatment will be oriented. In some methods, an arthroplasty jig may be used to position and orient a resection or sawing instrument, such as a cutting, drilling, reaming, or resurfacing instrument on the regions of the bone. The arthroplasty jig may, for example, include one or more apertures and/or slots that are configured to accept such an instrument. However, under some methods, it is difficult to determine the proper orientation of an arthroplasty jig and more specifically, of a unicompartmental arthroplasty jig. Some methods utilize customized arthroplasty jigs to provide orientation of the treatment relative to the regions of the bone. However, such jigs often rely on a human to subjectively determine or "eyeball" rotational angles and the extent of the treatment. For example, when performing a resection in a knee region of a patient femur and/or tibia, many jigs rely on a surgeon to determine the proper orientation of the jig as well as how much of the bone to remove. In other words, once a surgeon has begun cutting to perform a resection, it is often difficult to accurately stop the cut.

Accordingly, there is a need in the art for customized arthroplasty cutting guides and surgical methods of using such cutting guides that increases the accuracy of arthroplasty procedures.

BRIEF SUMMARY OF THE INVENTION

Implementations described and claimed herein address the foregoing problems by providing an arthroplasty cutting guide for making resections in a knee region of a patient femur in preparing a patient knee for the implantation of a femoral implant and a tibial implant.

The knee region includes surface topography including surface contours of a femoral condylar surface and a trochlear groove surface. In one implementation, the femoral implant includes: an articular condylar surface; a femur contacting side opposite the articular condylar surface and including a distal resection contacting surface, a posterior resection contacting surface, and a chamfer resection contacting surface. The femoral implant has a first distal-proximal thickness extending perpendicular from the distal resection contacting surface to the articular condylar surface. In one implementation, the tibial implant includes an articular plateau surface and a tibia contacting side, which includes a proximal resection contacting surface, opposite the articular plateau surface.

The tibial implant includes a second distal-proximal thickness extending perpendicular from the proximal resection contacting surface to the articular plateau surface.

In one implementation, the arthroplasty cutting guide comprises: a patient specific mating region, a distal resection slot, and a distal planar surface. The patient specific mating region is custom configured to interdigitate with the topography of the knee region and comprises surface contours that are a general negative image of the surface contours of the femoral condylar surface and the surface contours of the trochlear groove. The distal resection slot is configured to guide a distal resection in the knee region when the patient specific mating region interdigitates with the topography of the knee region such that the surface contours of the mating region make corresponding surface contact with the surface contours of the femoral condylar surface and the trochlear groove. The distal planar surface is parallel to the distal resection slot and is distally spaced apart from the distal resection surface by a distance equal to the sum of the first distal-proximal thickness of the femoral implant and the second distal-proximal thickness of the tibial implant.

Other implementations described and claimed herein provide an arthroplasty system for making resections in a knee region of a patient tibia in preparing a patient knee for the implantation of a tibial implant. The knee region includes surface topography including surface contours of a tibial plateau surface. In one implementation, the arthroplasty system comprises a cutting guide and an anchor pin.

The cutting guide comprises a patient specific mating region, a proximal resection slot, and an anchor pin hole. The patient specific mating region is custom configured to interdigitate with the topography of the knee region and comprises surface contours that are a general negative image of the surface contours of the tibial plateau surface. The proximal resection slot comprises an exterior opening defined in an exterior anterior surface of the cutting guide. The proximal resection slot extends anterior-posterior and medial-lateral in the cutting guide and is configured to guide a proximal resection in the knee region when the patient specific mating region interdigitates with the topography of the knee region such that the surface contours of the mating region make corresponding surface contact with the surface contours of the tibial plateau surface. The anchor pin hole comprises an exterior opening defined in the exterior anterior surface of the cutting guide. The anchor pin hole extends generally anterior-posterior through the cutting guide and intersects the proximal resection slot near a medial or lateral edge of the proximal resection slot. The anchor pin comprises an elongated shaft configured to be received in the anchor pin hole in securing the cutting guide to the patient tibia.

Other implementations described and claimed herein provide methods of performing a knee arthroplasty. In one implementation, a tibia cutting guide is placed a tibial plateau of a patient tibia. The tibia cutting guide includes a patient specific mating region, a proximal resection slot, and an anchor pin hole. The patient specific mating region is custom configured to interdigitate with a topography of the tibial plateau and comprises surface contours that are a general negative image of surface contours of the tibial plateau. The proximal resection slot comprises an exterior opening defined in an exterior anterior surface of the cutting guide, and the proximal resection slot extends anterior-posterior and medial-lateral in the cutting guide. The anchor pin hole comprises an exterior opening defined in the exterior anterior surface of the cutting guide, and the anchor pin hole extends generally anterior-posterior through the cutting guide, intersecting the proximal resection slot near a medial or lateral edge of the proximal resection slot. The patient specific mating region is caused to interdigitate with the topography of the tibial plateau. The anchor pin is inserted into the patient tibia via the anchor pin hole such that the anchor pin is present within both the anchor pin hole and the patient tibia. With the mating region interdigitated with the topography of the tibial plateau, a proximal resection of the patient tibia is made via the proximal resection slot.

In another implementation, a proximal resection is created a patient tibia near a tibial plateau of the patient tibia. A femoral cutting guide is placed on a condylar region of a patient femur. The femoral cutting guide includes a patient specific mating region, a distal resection slot, and a distal planar surface. The patient specific mating region is custom configured to interdigitate with a topography of the condylar region and comprises surface contours that are a general negative image of surface contours of the condylar region. The distal resection slot comprises an exterior opening defined in an exterior anterior surface of the cutting guide, and the distal resection slot extends anterior-posterior and medial-lateral in the cutting guide. The distal planar surface is parallel to the distal resection slot and distally spaced apart from the distal resection surface. The patient specific mating region is caused to interdigitate with the topography of the condylar region. With the patient specific mating region intedigitated with the topography of the condylar region, the distal planar surface is caused to abut against the proximal resection.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 1 is an isometric view of femoral and tibial unicompartmental implants interfaced with each other.

FIGS. 2B and 2C show the tibia cutting guide and the tibia of FIG. 2A with the tibia cutting guide interdigitated with the tibia.

FIG. 6 depicts an anterior elevation view of the tibia of FIG. 5 with the anchor pin removed.

DETAILED DESCRIPTION

Figure 2A:
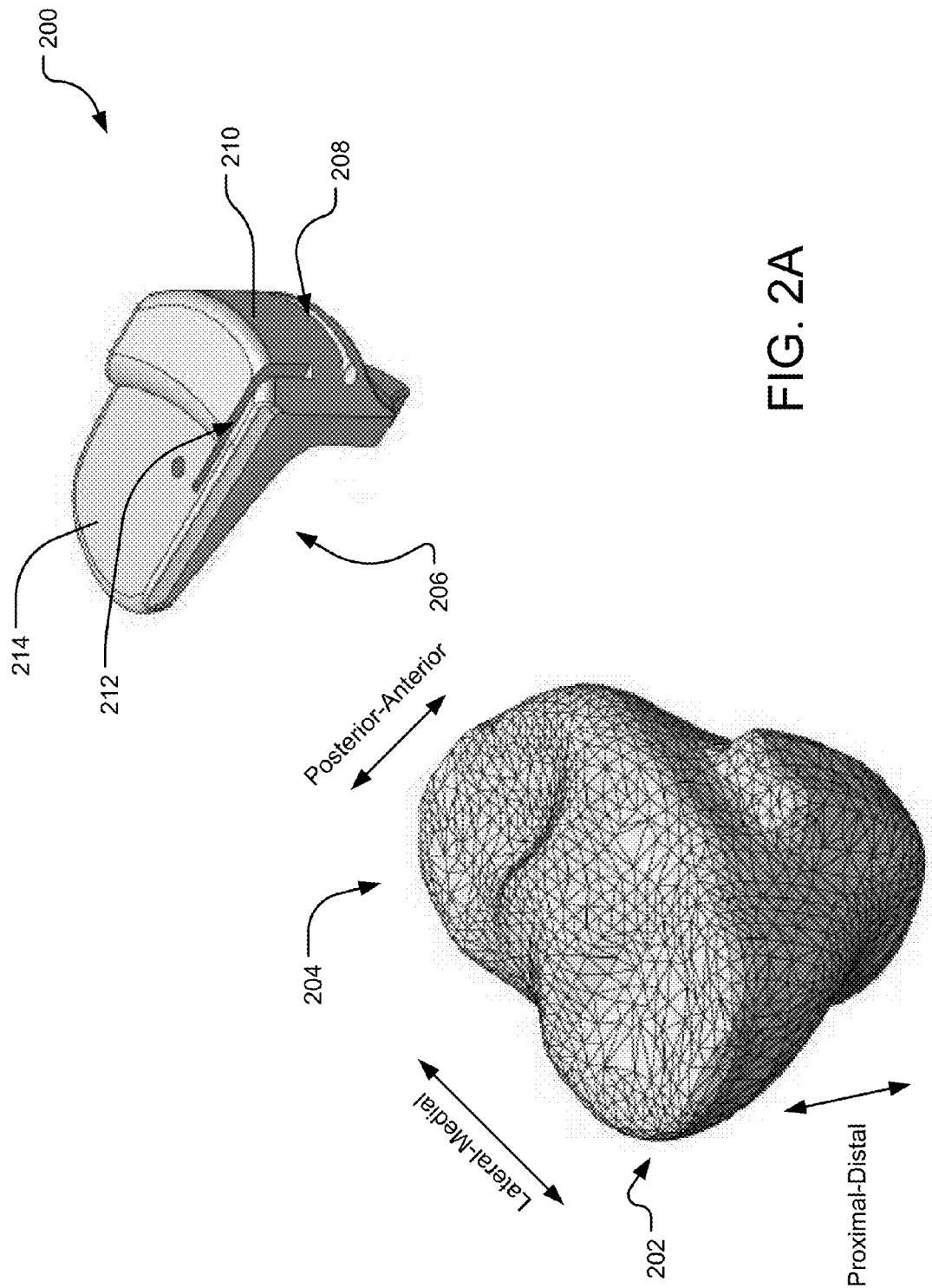
FIG. 2A illustrates an example tibia cutting guide and proximal tibia plateau.

Aspects of the presently disclosed technology involve customized unicompartmental arthroplasty cutting guides and methods of using the same during arthroplasty procedures. In one aspect, the cutting guides are customized to fit specific bone surfaces of a joint (e.g., knee, elbow, ankle, wrist, hip, shoulder, skull/vertebrae, vertebrae/vertebrae interface, etc.) of a specific patient to treat (e.g., cut, drilled, reamed, and/or resurfaced) the bone to provide one or more surfaces that can align with an implant and thereby accommodate the implant. In some aspects, depending on the implementation, both the implant and the cutting guide are automatically planned and generated according to the systems, apparatuses, and methods similar to those disclosed in U.S. patent application Ser. No. 12/636,939 to Park et al., entitled "Unicompartmental Customized Arthroplasty Cutting Jigs and Methods of Making the Same and filed on Dec. 14, 2009, which is incorporated by reference in its entirety into this Detailed Description.

For an overview discussion of the implants for which bone surfaces in a knee area are treated to align with and accommodate, reference is made to FIG. 1, which illustrates an isometric view of a femoral unicompartmental implant 100 interfaced with a tibial unicompartmental implant 102.

In one implementation, the femoral implant 100 includes an articular condylar surface 104 and a femur contacting side 106 opposite the articular condylar surface 104. The femur contacting side 106 includes one or more surfaces each adapted to contact or otherwise engage a bone surface in a patient femur. In one implementation, the femur contacting side 106 includes a distal resection contacting surface 108, a chamfer resection contacting surface 110, and a posterior resection contacting surface 112, which are adapted to engage a distal resection, chamfer resection, and a posterior resection in the patient femur that are made using a femoral cutting guide as described herein. The femoral implant 100 includes a distal-proximal thickness 114 extending perpendicular from the distal resection contacting surface 108 to the articular condylar surface 104.

Similarly, in one implementation, the tibial implant 102 includes an articular plateau surface 116 and a tibia contacting side 118. The tibia contacting side 118 includes one or more surfaces, each of which is adapted to contact or otherwise engage a bone surface in a patient tibia. In one implementation, the tibia contacting side 118 includes a proximal resection contacting surface 120, which is adapted to engage a proximal resection in the patient tibia that is made using a tibial cutting guide as described herein. The tibial implant 102 includes a distal-proximal thickness 122 extending perpendicular from the proximal resection contacting surface 120 to the articular plateau surface 116.

Prior to implantation of the femoral implant 100 or the tibial implant 102, the damaged region in the femur or the tibia, respectively, is prepared to receive the implant. Stated differently, the femur or the tibia is treated (e.g., cut, drilled, reamed, and/or resurfaced) using an arthroplasty cutting guide to provide one or more resections that can align and mate with corresponding surfaces of the implant 100 or 102 and thereby accommodate the implant 100 or 102.

For a detailed discussion of an arthroplasty system for making resections in a knee region to prepare a patient knee for the implantation of the tibial implant 102, reference is made to FIG. 2A, which shows a tibia cutting guide 200 and a patient tibia 202 in the patient knee. As can be understood from FIG. 2A, the patient tibia 202 includes a surface topology including surface contours of a tibial plateau surface 204.

In one implementation, the tibia cutting guide 200 is custom generated to allow a surgeon to accurately and quickly perform an arthroplasty procedure. In other words, the tibia cutting guide 200 includes a patient specific mating region 206 configured to interdigitate with the topography of the knee region. The patient specific mating region 206 includes surface contours that are a general negative image of the surface contours of the tibial plateau surface 204.

The tibia cutting guide 200 includes a proximal resection slot 208 defined in an exterior anterior surface 210 and a vertical resection slot 212 defined in an exterior proximal surface 214. The proximal resection slot 208 is configured to guide a proximal resection in the tibia 202, and the vertical resection slot 212 is configured to guide at least a beginning of a vertical (i.e., distal-proximal) resection in the tibia 202.

As can be understood from FIGS. 2B and 2C, when the tibia cutting guide 200 is used during an arthroplasty procedure, the patient specific mating region 206 interdigitates with the topography of the knee region such that the surface contours of the patient specific mating region 206 make corresponding surface contact with the surface contours of the tibial plateau surface 204. As such, when the surface topography of the knee region is received into the patient specific mating region 206, the surfaces 204 and 206 matingly match, thereby increasing stability during and accuracy of the arthroplasty procedure.

Figure 3A:
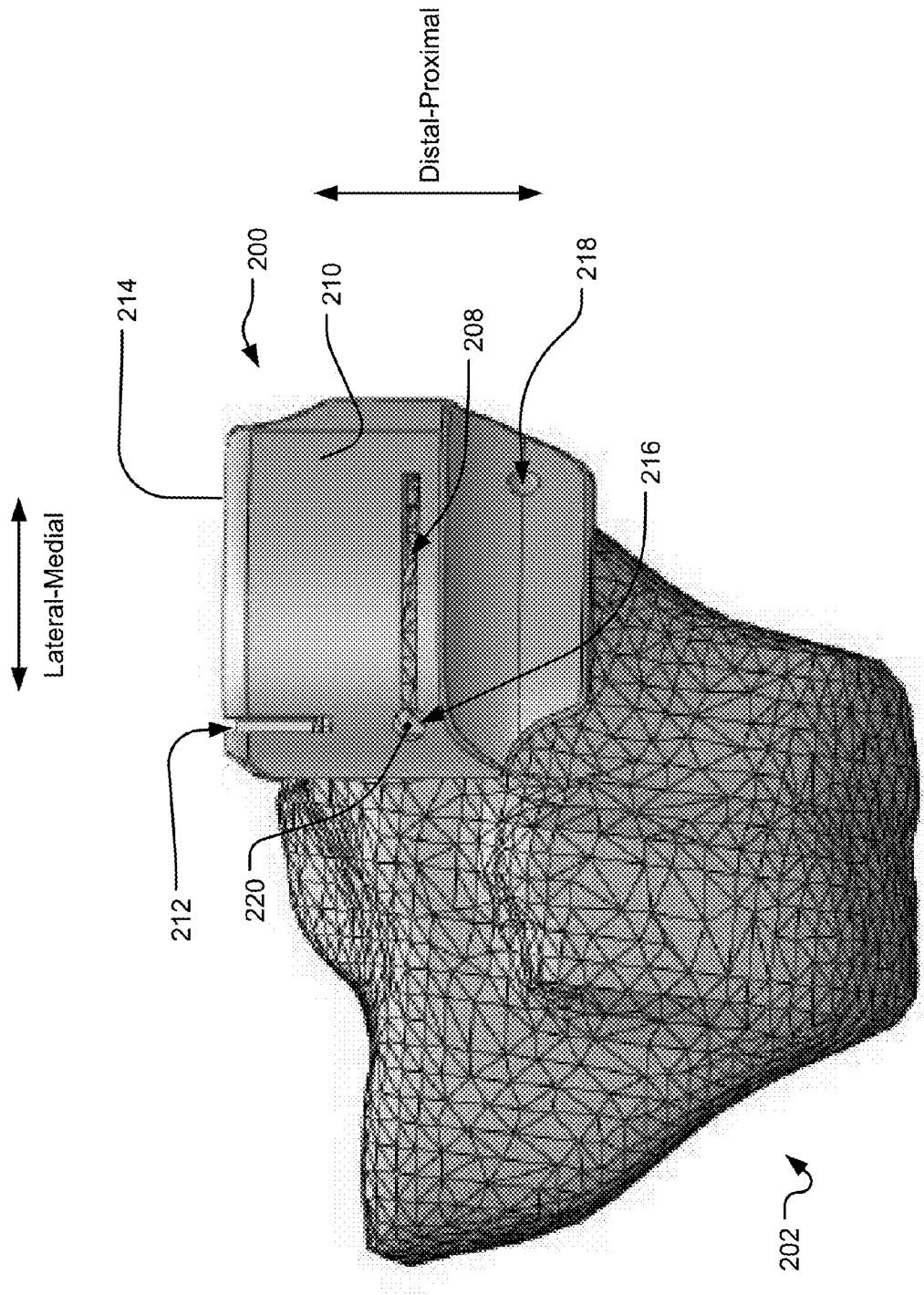
FIGS. 3A and 3B show side and top views, respectively, of the interdigitated tibia cutting guide of FIG. 2A.
Figure 3B:
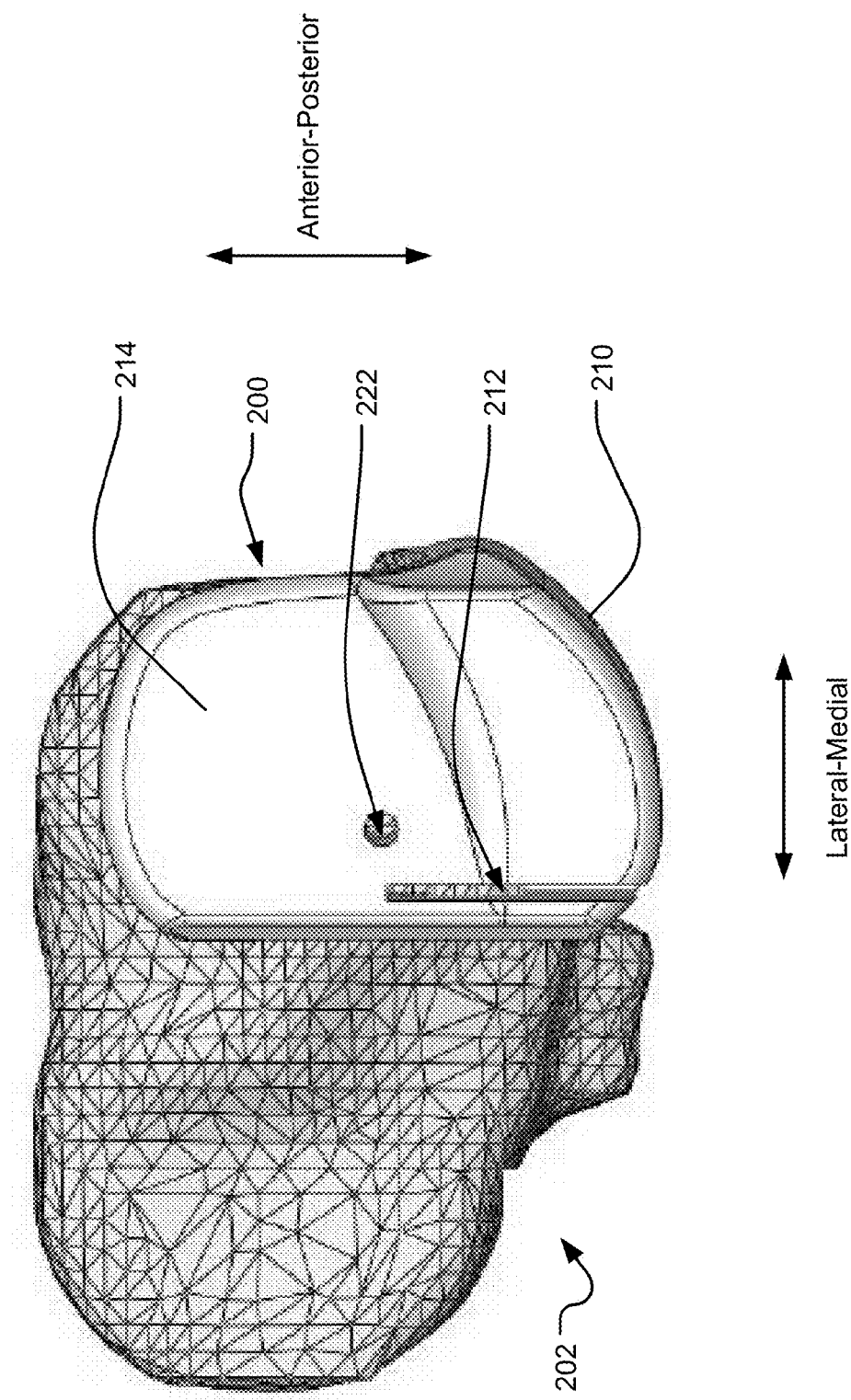

Turning to FIGS. 3A and 3B, which are side and top views, respectively, of the tibia cutting guide 200 interdigitated with the tibia 202, it will be understood that in one implementation, the proximal resection slot 208 is an exterior opening extending anterior-posterior and medial-lateral in the tibia cutting guide 200, and the vertical resection slot 212 is an exterior opening extending anterior-posterior and distal-proximal in the tibia cutting guide 200. The exterior openings are adapted to receive and guide a resection or sawing instrument to perform proximal and vertical resections of the tibia 202.

The tibia cutting guide 200 is configured to assist a surgeon during the performance of such resections by increasing, for example, accuracy and stability. To achieve this, in one implementation, the tibia cutting guide 200 includes one or more anchor pin holes 216, 218, and 222 including exterior openings that are adapted to receive an elongated shaft of an anchor pin 228 (shown in FIG. 4) in an interference fit (e.g., using friction) to secure the tibia cutting guide 200 to the patient tibia 202. When the anchor pin 228 is inserted into the patient tibia 202 via one of the anchor pin holes 216, 218, or 222, the anchor pin 228 is present in both the anchor pin hole 216, 218, or 222 and the patient tibia 202. In one implementation, the anchor pin holes include an anterior pin hole 216 defined in the exterior anterior surface 210, a medial/lateral pin hole 218 defined in the exterior anterior surface 210, and a proximal pin hole 222 defined in the exterior proximal surface 214.

The anterior pin hole 216 extends generally anterior-posterior through the tibia cutting guide 200. As shown in the example in FIGS. 3A and 3B, the anterior pin hole 216 may be substantially coplanar with the proximal resection slot 208 and/or the vertical resection slot 212. The anterior pin hole 216 includes a longitudinal center axis 220 positioned at the general center of the exterior opening of the anterior pin hole 216. In one implementation, the longitudinal center axis 220 is substantially centered distal-proximal relative to a distal-proximal thickness of the proximal resection slot 208 and medial-lateral relative to a medial-lateral thickness of the vertical resection slot 212.

The characteristics of the proximal resection slot 208 and the anterior pin hole 216 are configured to assist a surgeon during the performance of proximal resections. In one implementation, the anterior pin hole 216 intersects with the proximal resection slot 208 near a medial or lateral edge of the proximal resection slot 208 such that the anterior pin hole 216 defines the medial or lateral edge of the proximal resection slot 208. When the proximal resection is performed, the surgeon begins the proximal resection until the anchor pin in the proximal pin hole 222 is reached, which is removed to complete the proximal resection. At the end of the proximal resection, the anchor pin 228 in the anterior pin hole 216 serves as a sawing stop to prevent the surgeon from cutting too far into the tibia 202. As such, the anchor pin 228 is made from a material that is harder and more saw resistant than a material of the tibia cutting guide 200 around a border of the proximal resection slot 208. For example, the anchor pin 228 may be made from a metal or ceramic, and the material bordering the proximal resection slot in the tibia cutting guide 200 may be made from a polymer.

In some implementations, the anchor pin 228 in the anterior pin hole 216 may serve as a sawing stop during a vertical resection while the tibia cutting guide 200 is interdigitated with the topography of the tibial plateau surface 204. In other implementations, the anterior pin hole 216 and the vertical resection slot 212 do not intersect. Accordingly, at least a beginning of the vertical resection is performed using the vertical resection slot 212. In other words, a vertical resection line is scored using the vertical resection slot 212.

Figure 4:
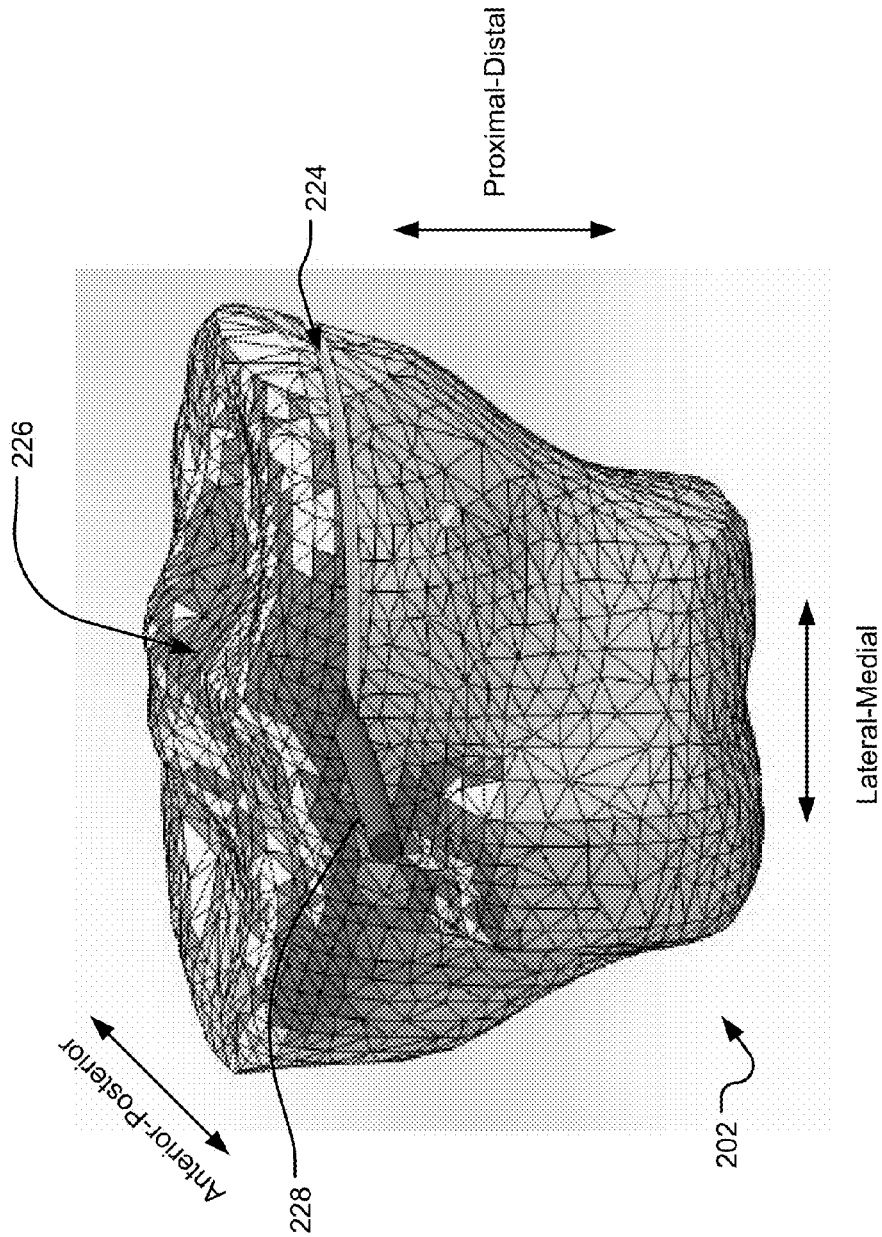
FIG. 4 illustrates a proximal resection of and a vertical score in the tibia with an anchor pin inserted.
Figure 5:
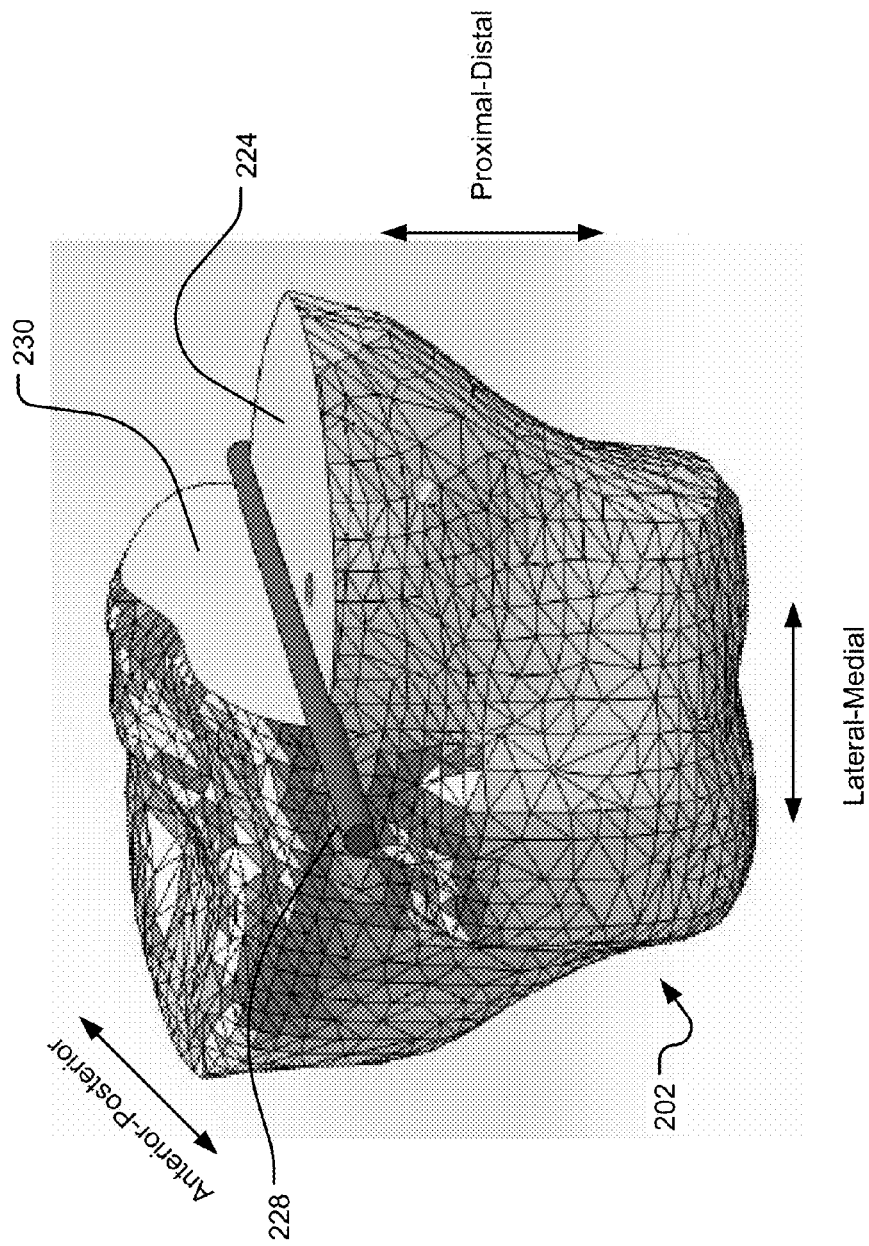
FIG. 5 is the same view as FIG. 4 with the vertical resection of the tibia completed.

Turning to FIG. 4, after making the proximal resection 224 and scoring the vertical resection line 226, the anchor pin 228 and the tibia cutting guide 200 may be removed from the tibia 202. The anchor pin 228 is then reinserted into a hole in the patient tibia that was formerly occupied by the anchor pin 228 when the anchor pin 228 was inserted through the anterior pin hole 216 into the patient tibia 202. As can be understood from FIG. 5, in one implementation, the vertical resection 230 is completed using the anchor pin 228 as a guide and sawing stop without the tibia cutting guide 200 being mounted on the patient tibia 202. Using the anchor pin 228 as a sawing stop for the proximal resection and/or the vertical resection, not only prevents the surgeon from cutting too far into the tibia 202, but stress risers that could otherwise cause a crack to propagate horizontally or vertically from a respective resection are substantially eliminated. As shown in FIG. 6, after the anchor pin 228 is removed, the proximal resection 224 and the vertical resection 230 are complete, and the tibia 202 is prepared to receive the tibial implant 102.

Figure 7A:
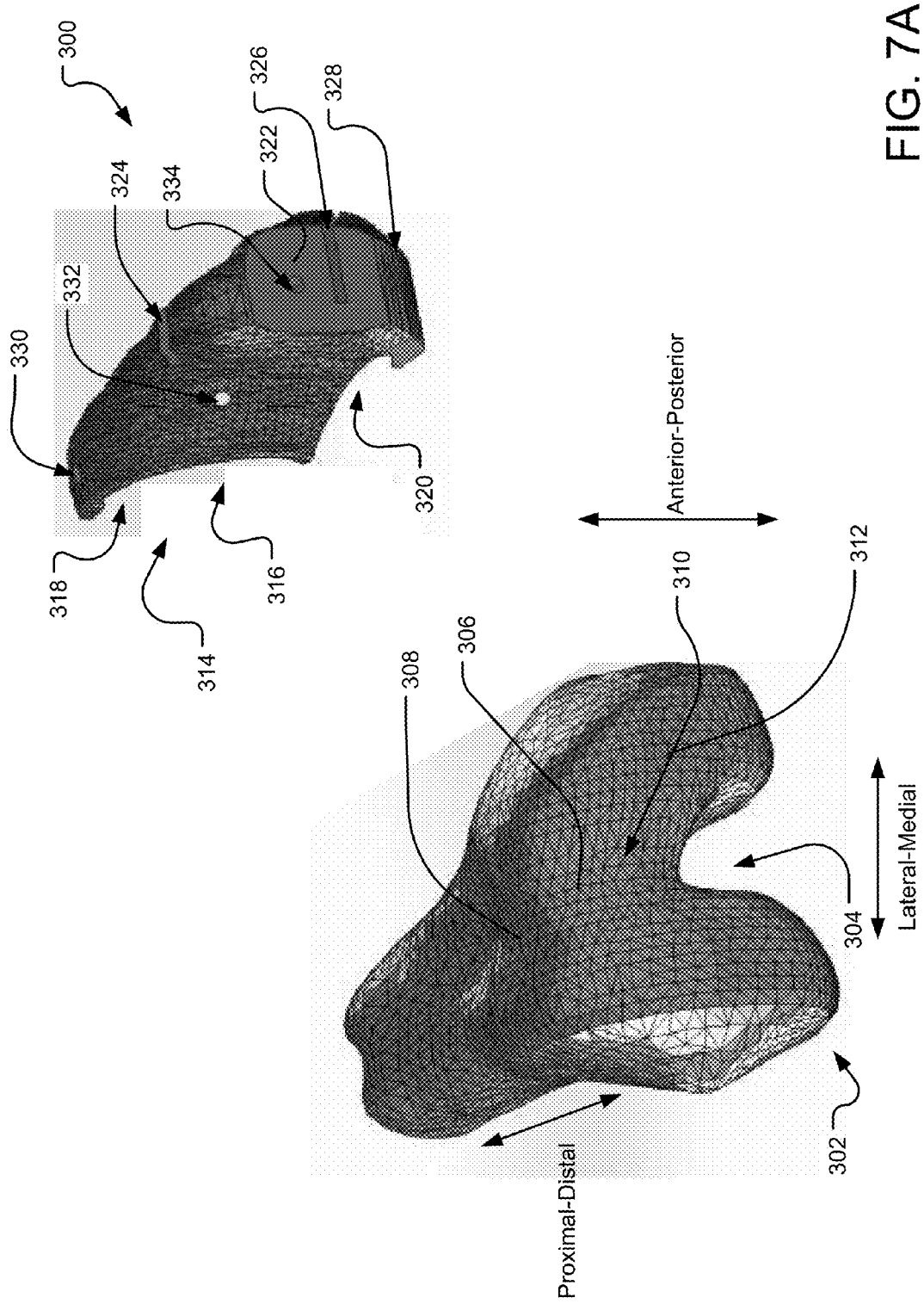
FIG. 7A shows an example femoral cutting guide and femur.

For a detailed discussion of an arthroplasty system for making resections in a knee region to prepare a patient knee for the implantation of the femoral implant 100, reference is made to FIG. 7A, which shows a femur cutting guide 300 and a patient femur 302 in the patient knee. The patient femur 302 includes a trochlear groove surface 304 having a distal trochlear groove 306 and an anterior trochlear groove 308. The patient femur 302 further includes a condylar surface 310 having a distal condyle 312. As can be understood from FIG. 7A, the femur 302 has a surface topography including surface contours of the condylar surface 310 and the trochlear groove surface 304.

The femur cutting guide 300 is custom generated to allow a surgeon to accurately and quickly perform an arthroplasty procedure. In other words, the femur cutting guide 300 includes a patient specific mating region 314 configured to interdigitate with the topography of the knee region. The patient specific mating region 314 includes surface contours that are a general negative image of the surface contours of the condylar surface 310 and the trochlear groove surface 304. In one implementation, the patient specific mating region 314 includes: a distal trochlear groove region 316 adapted to receive the distal trochlear groove 306; an anterior trochlear groove mating region 318 adapted to receive the anterior trochlear groove 308; and a distal condylar mating region 320 adapted to receive the distal condyle 312.

In one implementation, the femur cutting guide 300 includes a distal planar surface 322, a distal resection slot 324, a chamfer resection slot 326, a posterior resection slot 328, and one or more anchor pin holes 330, 332, and 334. The distal resection slot 324, the chamfer resection slot 326, and the posterior resection slot 328 are configured to guide a distal resection, chamfer resection, and posterior resection, respectively. In one implementation, the distal resection slot 324 is positioned generally parallel to the distal planar surface 322, and the chamfer resection slot 326 is defined in the distal planar surface 322. The posterior resection slot 328 is positioned generally perpendicular to the distal resection slot 324, and the chamfer resection slot 326 is positioned at angle (e.g., approximately 45 degrees) relative to the distal resection slot 324. In one implementation, the chamfer resection slot is further positioned at an angle (e.g., approximately 45 degrees) relative to the posterior resection slot 328. The angular relationship of the chamfer resection slot 326 to the distal resection slot 324 and/or the posterior resection slot 328 may be based on the geometry of the femoral implant 100, such as the distal resection contacting surface 108, the chamfer resection contacting surface 110, and the posterior resection contacting surface 112.

Figure 7B:
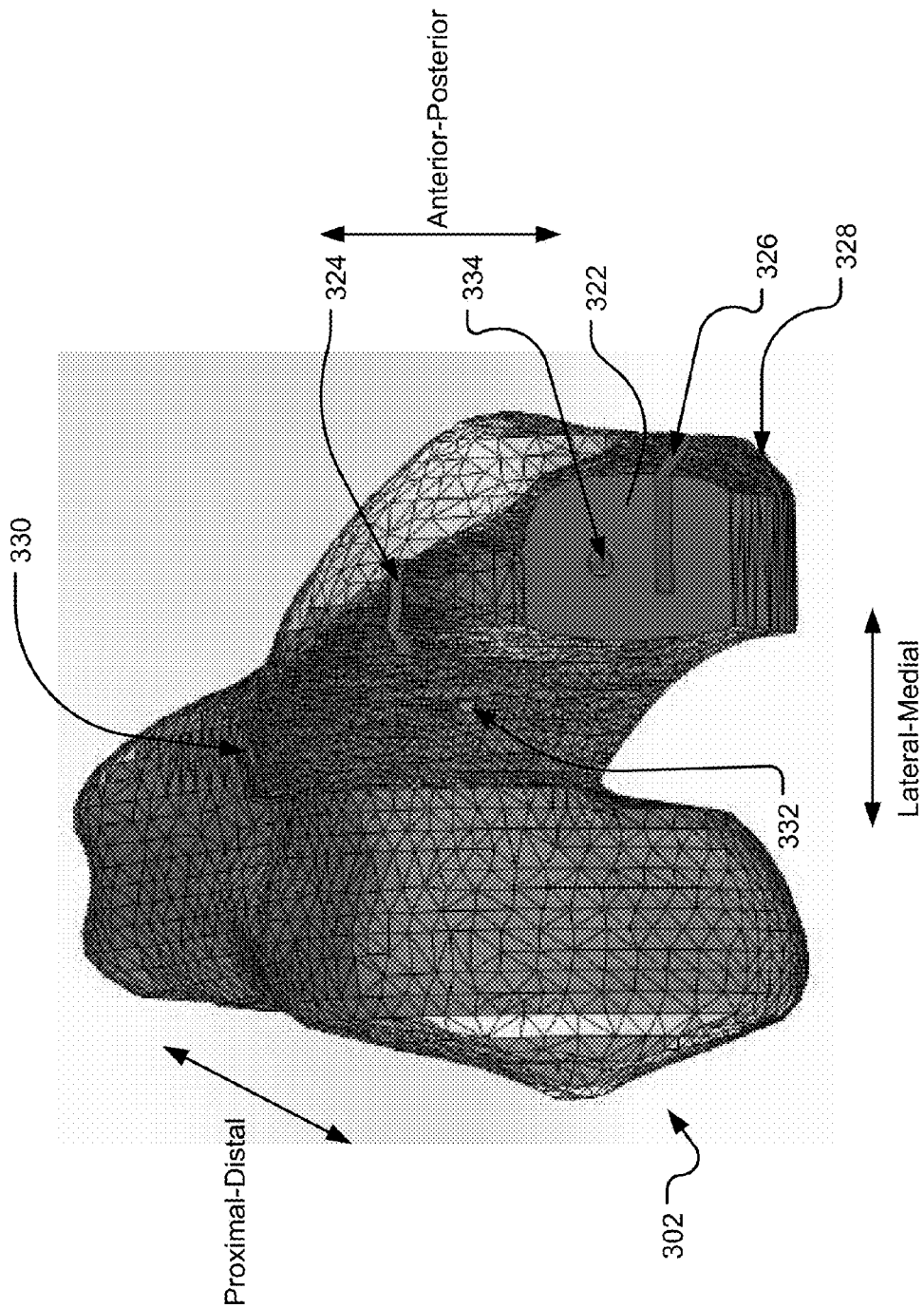
FIG. 7B illustrates the femoral cutting guide and the femur of FIG. 7A with the femoral cutting guide interdigitated with the femur.

As can be understood from FIG. 7B, when the femur cutting guide 300 is used during an arthroplasty procedure, the patient specific mating region 314 interdigitates with the topography of the knee region such that the surface contours of the patient specific mating region 314 make corresponding surface contact with the surface contours of the condylar surface 310 and the trochlear groove surface 304. As such, when the surface topography of the knee region is received into the patient specific mating region 314, the condylar surface 310 and the trochlear groove surface 304 matingly match with the patient specific mating region 314, thereby increasing stability during and accuracy of the arthroplasty procedure.

Figure 8:
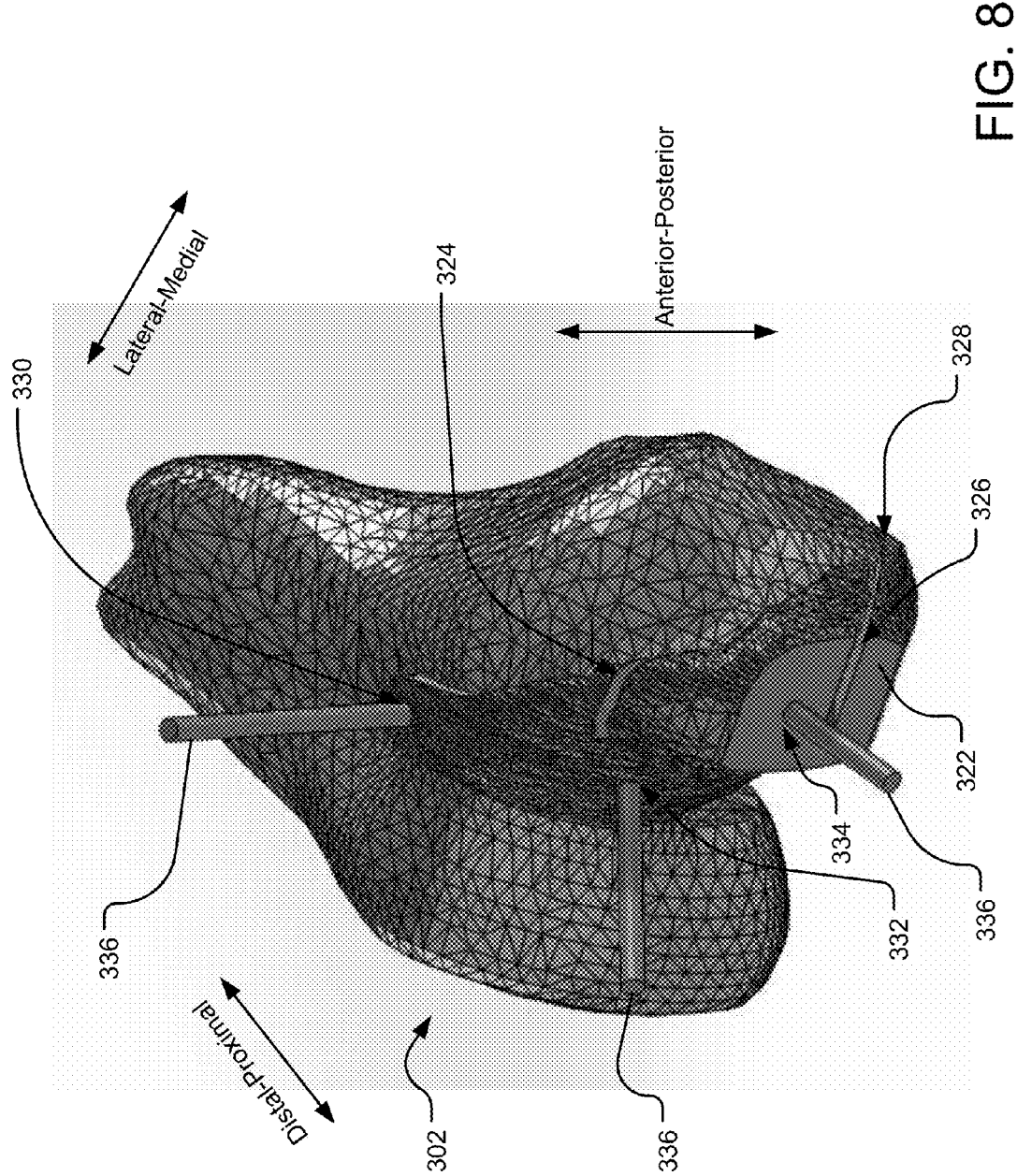
FIG. 8 shows a side perspective view of the interdigitated femoral cutting guide of FIG. 7B with anchor pins inserted.

Turning to FIG. 8, the femur cutting guide 300 is fixed into place on the patient femur 302 using anchor pins 336. In one implementation, one of the anchor pins 336 is inserted into the patient femur 302 via the first anchor pin hole 330, which extends through the anterior trochlear groove mating region 318 in a direction generally parallel to the distal resection slot 324. Another of the anchor pins 336 is inserted into the patient femur 302 via the second anchor pin hole 332, which extends through the distal trochlear mating region 316 in a direction angled relative the distal resection slot 324. Yet another of the anchor pins 336 is inserted into the patient femur 302 via the third anchor pin hole 334, which extends through the distal condylar mating region 320 in a direction generally perpendicular relative to the distal resection slot 324.

Figure 9:
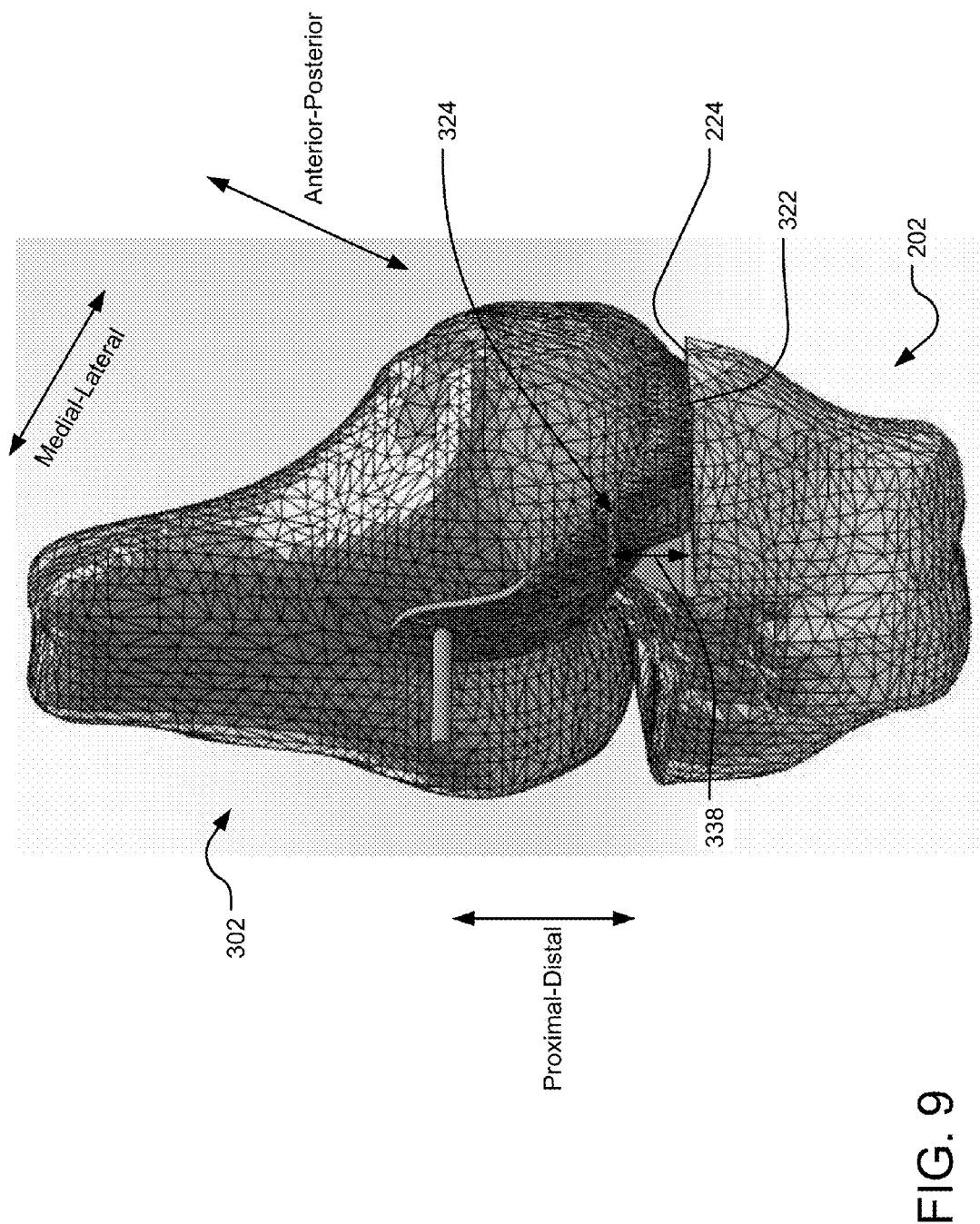
FIG. 9 illustrates a distal plane of the femoral cutting guide in planar contact with the proximal resection of the tibia.

As can be understood from FIG. 9, in one implementation, before performing the distal, chamfer, and/or posterior resections, ligament balance may be checked by placing the distal planar surface 322 in planar contact with the proximal resection 224 of the patient tibia 202. While the distal planar surface 322 is in such planar contact with the proximal resection 224, the femoral cutting guide 300 is engaged with the condylar surface 310 of the patient femur 302 and with the proximal resection 224 of the patient tibia 202. In one implementation, the distal planar surface 322 is distally spaced apart from the distal resection slot 324 by a distance 338 equal to a sum of the first and second distal-proximal thicknesses 114 and 122 of the femoral and tibial implants 100 and 102 (see FIG. 1). As such, by checking the ligament balance using the femur cutting guide 200, it may be verified that the ligament balance will be achieved with the implants 100 and 102.

Figure 10A:
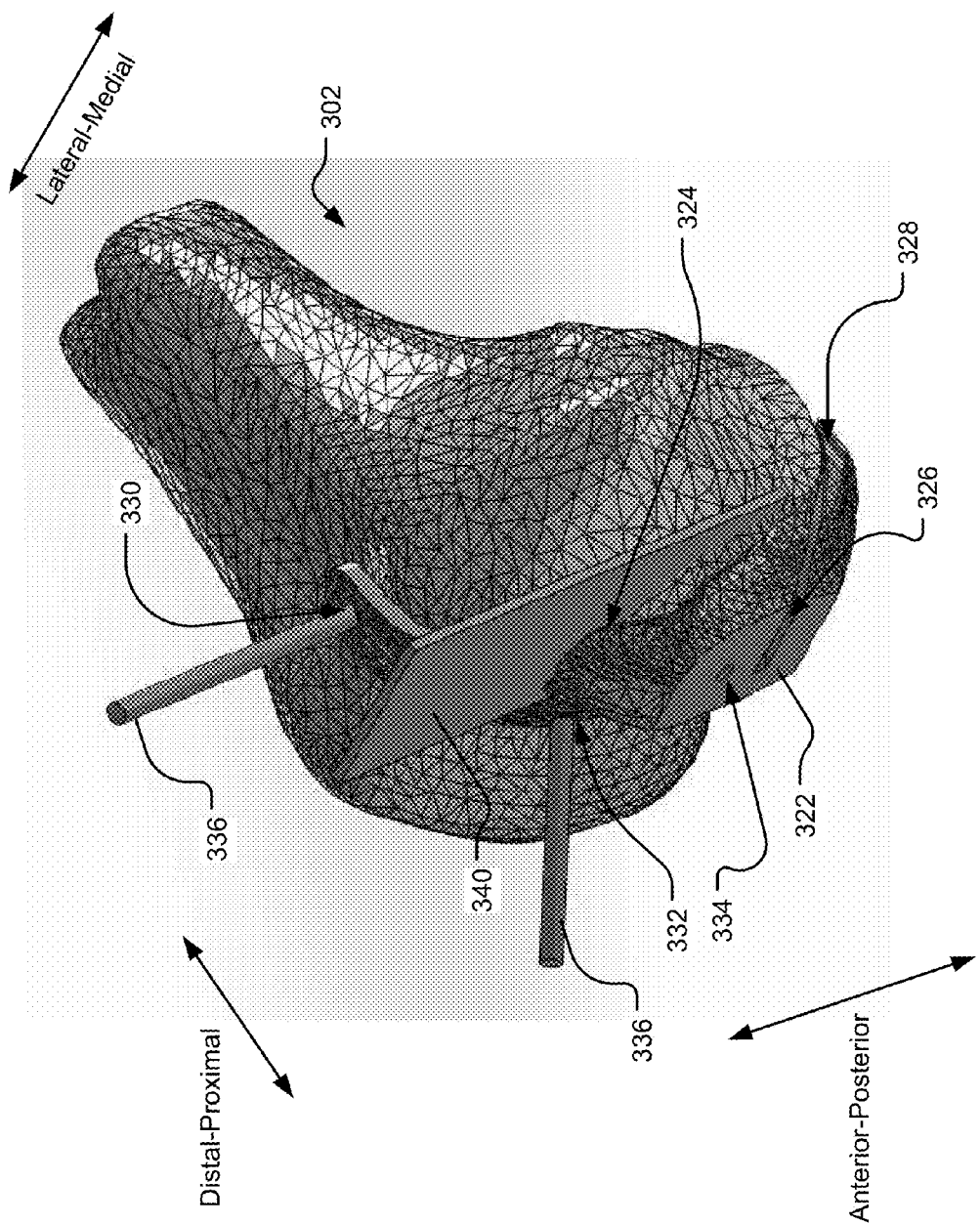
FIG. 10A shows a side perspective view of the interdigitated femoral cutting guide of FIG. 7B with a resection or sawing instrument inserted into a distal resection slot.
Figure 10B:
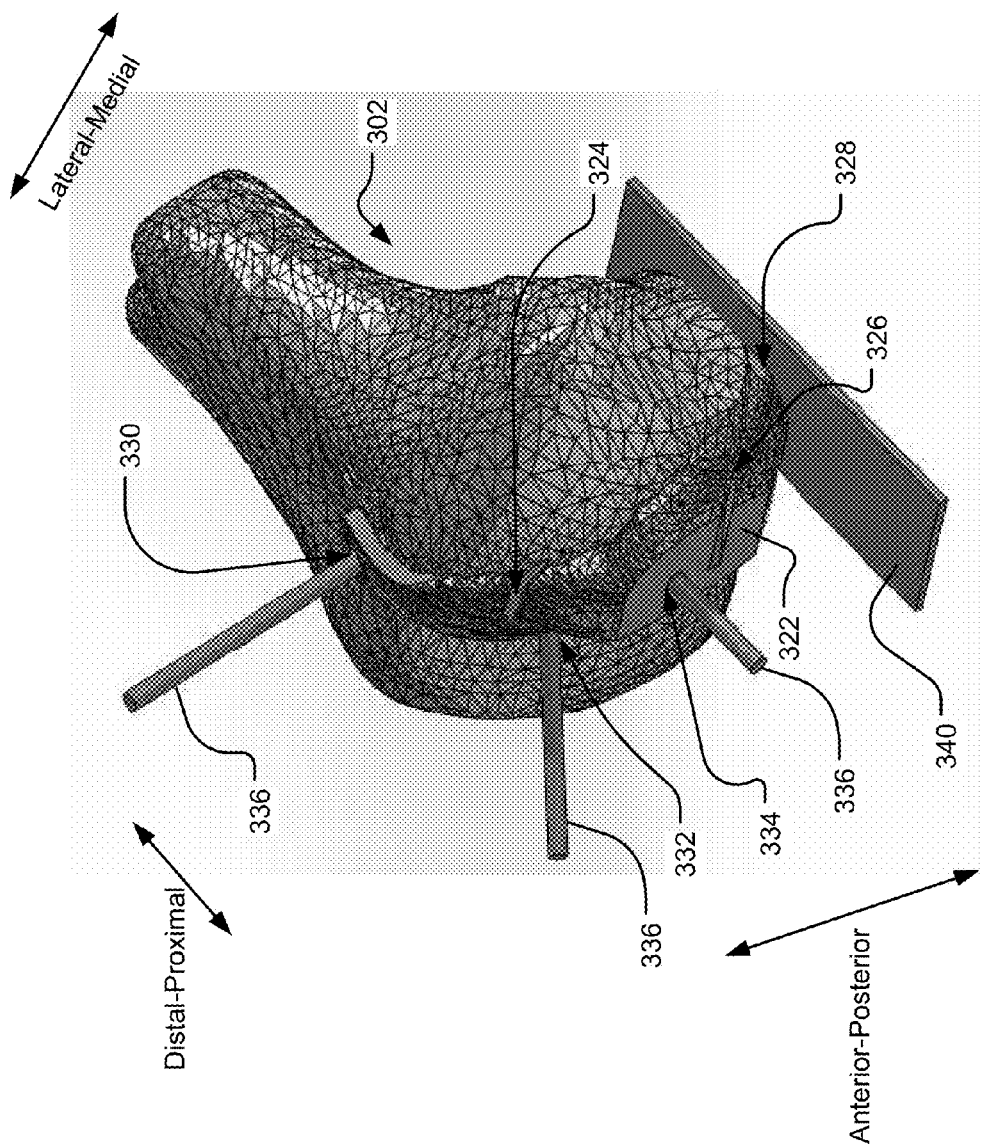
FIG. 10B depicts the same view as FIG. 10A with the resection or sawing instrument inserted into a posterior resection slot.
Figure 10C:
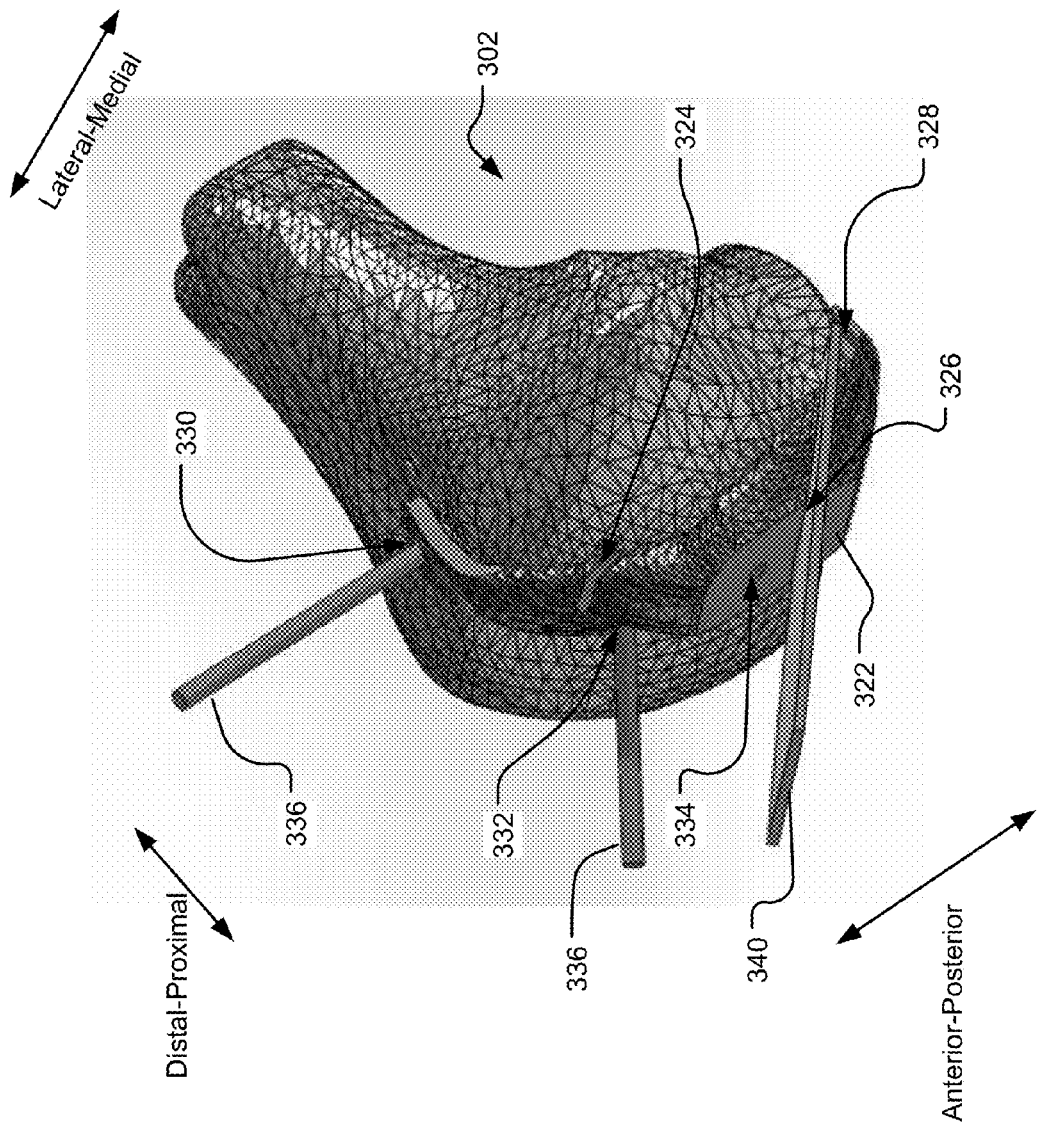
FIG. 10C depicts the same view as FIG. 10A with the resection or sawing instrument inserted into a chamfer resection slot.

Referring to FIGS. 10A-10C, which show a resection or sawing instrument 340 inserted into the distal resection slot 324, the posterior resection slot 328, and the chamfer resection slot 326, respectively, after checking the ligament balance, the knee is flexed to make resections in the femur 302. The distal resection slot 324 guides the distal resection of the patient femur 302, the posterior resection slot 328 guides the posterior resection of the patient femur 302, and the chamfer resection slot 326 guides the chamfer resection of the patient femur 302.

Figure 11:
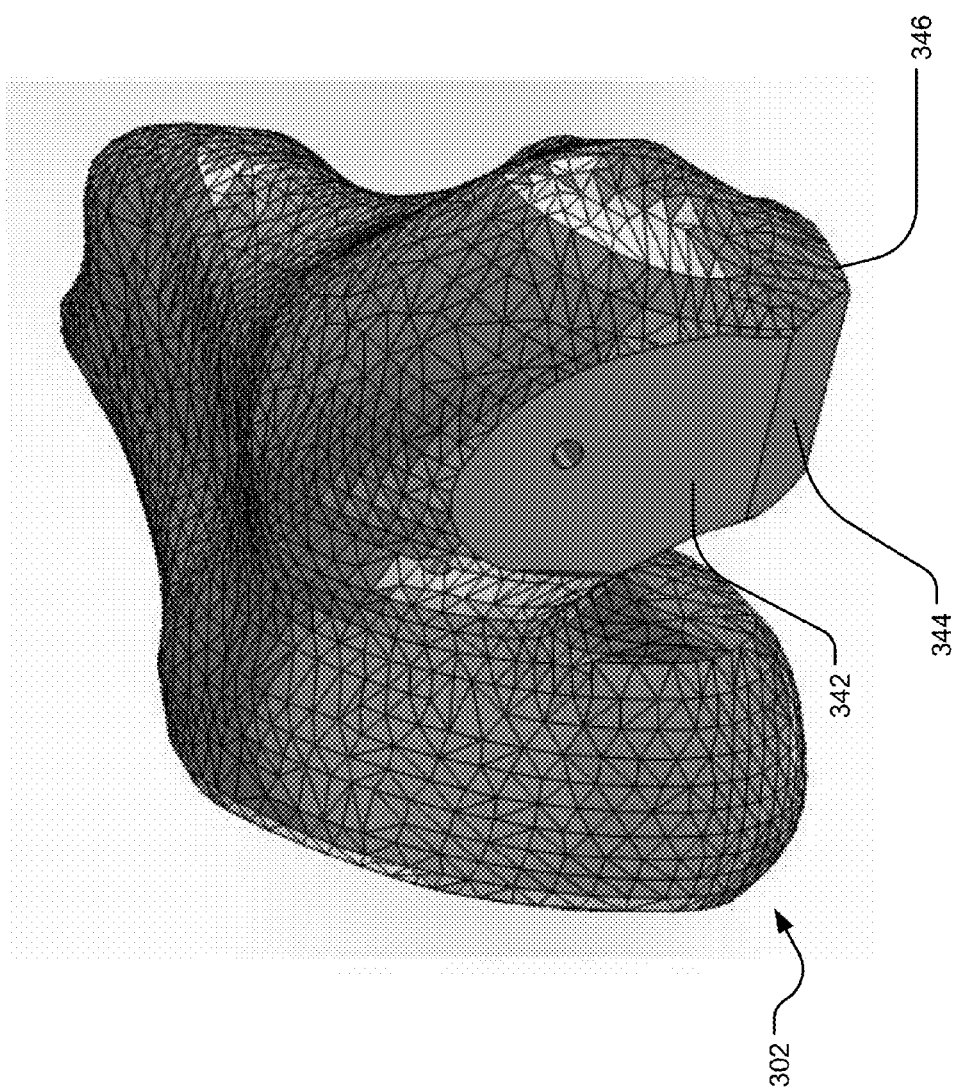
FIG. 11 shows a distal resection, a posterior resection, and a chamfer resection of the femur.
Figure 12:
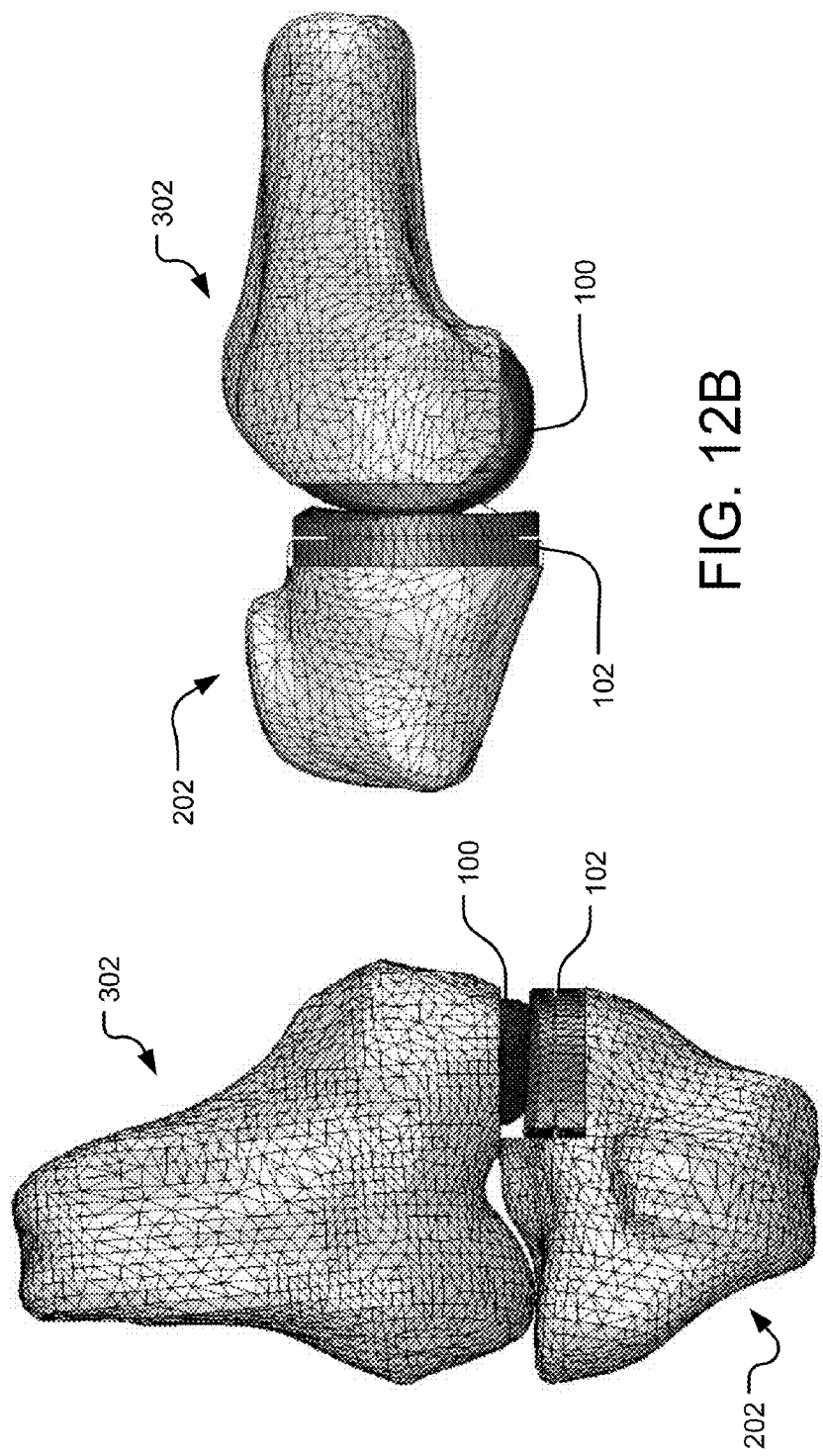
FIGS. 12A and 12B illustrate a coronal view and a sagittal view of the knee joint, respectively, showing trialing of the femoral and tibial implants.

As shown in FIG. 11, after the femur cutting guide 300 is removed, a distal resection 342, a chamfer resection 344, and a posterior resection 346 are complete, and the femur 302 is prepared to receive the femoral implant 100. After the femoral and tibial implants 100 and 102 are implanted on the femur 302 and tibia 202, respectively, trialing of the femoral and tibial implants 100 and 102 may be performed, as shown in FIGS. 12A and 12B.

Figure 13:
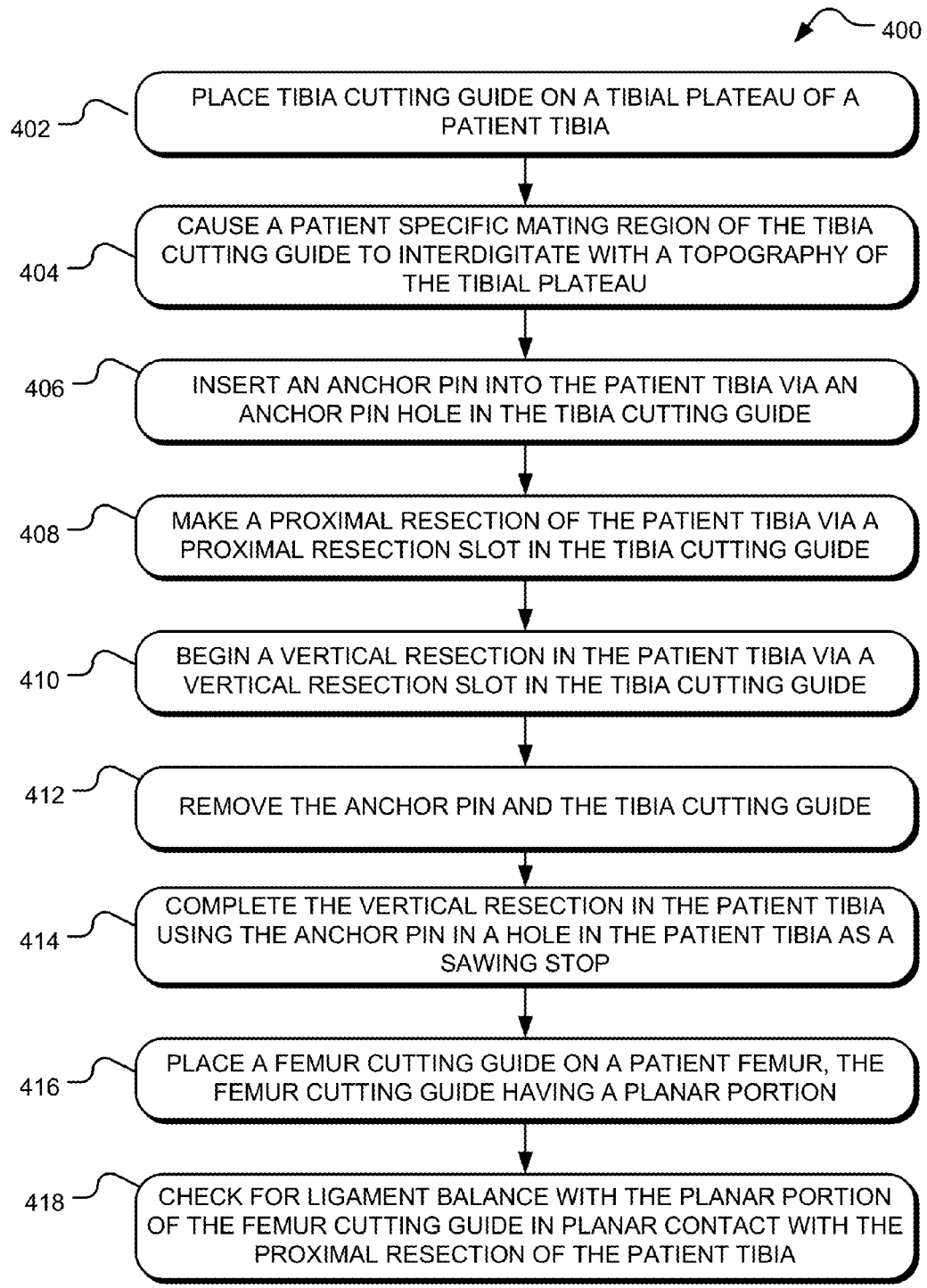
FIG. 13 is a flow chart showing example operations for performing treatment of the tibia for the tibial implant and of the femur for checking for ligament balance.

Turning to FIG. 13, example operations 400 for performing treatment of the tibia for the tibial implant and of the femur for checking for ligament balance are shown. A placing operation 402 places a tibia cutting guide on a tibial plateau of a patient tibia. In one implementation, the tibia cutting guide includes a patient specific mating region custom configured to interdigitate with a topography of the tibial plateau. To achieve this, the patient specific mating region may have surface contours that are a general negative image of surface contours of the tibial plateau.

The tibia cutting guide further includes a proximal resection slot and an anchor pin hole. In one implementation, the proximal resection slot includes an exterior opening that is defined in an exterior anterior surface of the tibia cutting guide. The proximal resection slot extends anterior-posterior and medial-lateral in the tibia cutting guide such that the proximal resection slot is configured to guide a proximal resection. In one implementation, the anchor pin hole includes an exterior opening that is defined in the exterior anterior surface of the tibia cutting guide. The anchor pin hole extends generally anterior-posterior through the tibia cutting guide and intersects with the proximal resection slot near a medial or later edge of the proximal resection slot. In one implementation, the tibia cutting guide includes a vertical resection slot having an exterior opening extending anterior-posterior and distal-proximal in the tibia cutting guide.

A causing operation 404 causes the patient specific mating region of the tibia cutting guide to interdigitate with the topography of the tibial plateau. An inserting operation 406 inserts an anchor pin into the patient tibia via the anchor pin hole such that the anchor pin is present within both the anchor pin hole and the patient tibia. With the patient specific mating region interdigitated with the topography of the tibial plateau, a making operation 408 makes a proximal resection of the patient tibia via the proximal resection slot. In one implementation, the making operation 408 uses the anchor pin as a sawing stop.

In one implementation, a beginning operation 410 at least begins a vertical resection in the patient tibia via the vertical resection slot. For example, the beginning operation 410 scores a vertical resection line in the patient tibia using the vertical resection slot as guidance. Once the making operation 408 and/or the beginning operation 410 are complete, a removing operation 412 removes the anchor pin from the tibia cutting guide. In one implementation, the removing operation 412 further removes the tibia cutting guide from the tibial plateau. A completing operation 414 reinserts the anchor pin into a hole in the patient tibia formerly occupied by the anchor pin when the anchor pin was present in both the anchor pin hole and the patient tibia. In one implementation, the completing operation 414 completes the vertical resection without the tibia cutting guide mounted on the patient tibia by using the anchor pin as a sawing stop. It will be appreciated by those skilled in the art that the completing operation 414 may comprise completing the proximal resection without the tibia cutting guide mounted on the patient tibia by using the anchor pin as a sawing stop in other implementations.

A placing operation 416 places a femur cutting guide on a condylar region of a patient femur. In one implementation, the femur cutting guide includes a custom mating region having a topography that makes interdigitating surface engagement with a topography of the condylar region. The femur cutting guide further includes a planar portion generally parallel with and distally offset from a distal resection slot of the femur cutting guide. A checking operation 418 places the planar portion of the femur cutting guide in planar contact with the proximal resection made during the making operation 408. The checking operation 418 checks for ligament balance with the planar portion in planar contact with the proximal resection.

Figure 14:
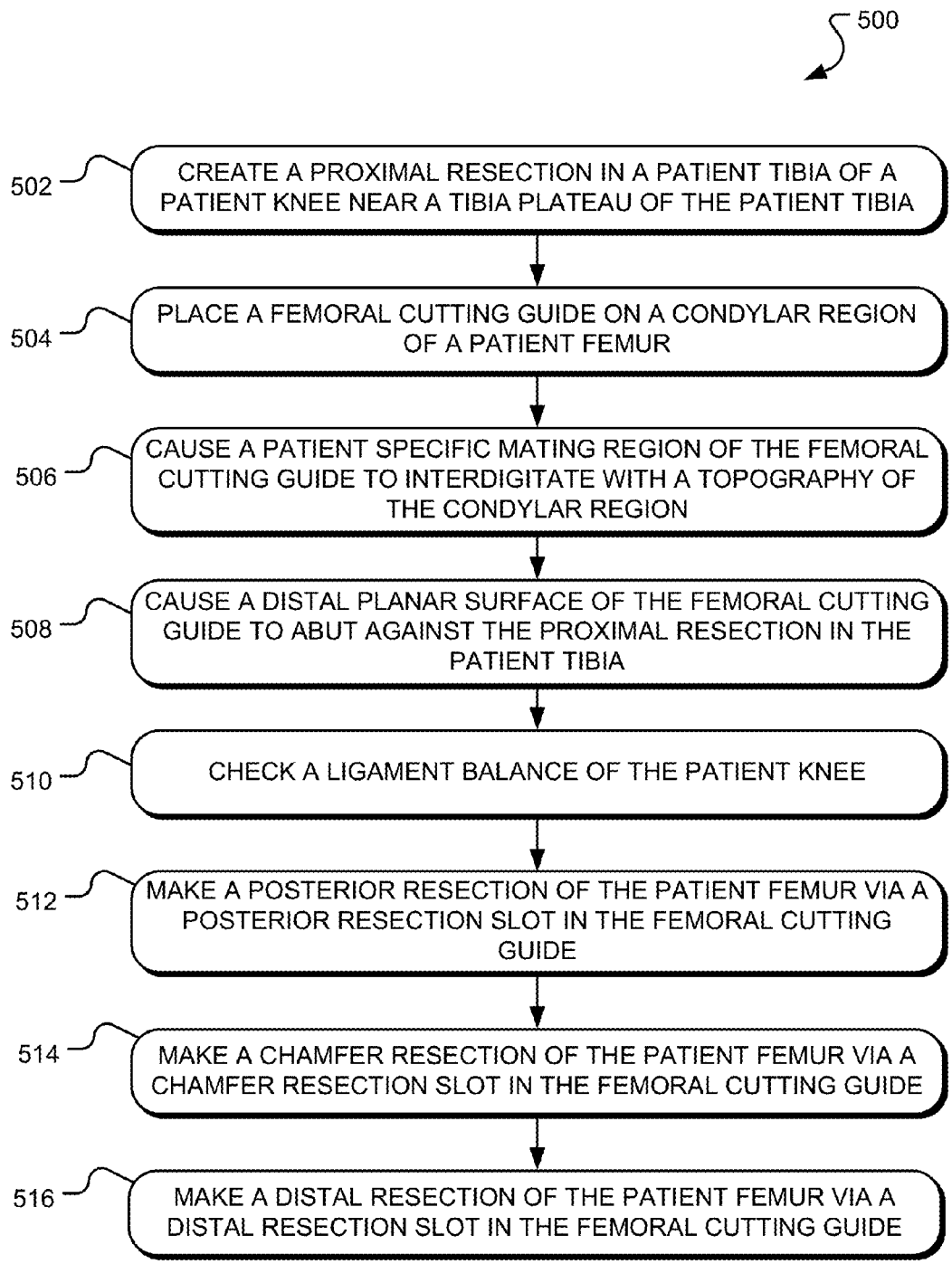
FIG. 14 is a flow chart showing example operations for performing treatment of the femur for the femoral implant.

FIG. 14 is a flow chart showing example operations 500 for performing treatment of the femur for the femoral implant. In one implementation, a creating operation 502 creates a proximal resection in a patient tibia near a tibial plateau of the patient tibia. For example, the creating operation 502 may create the proximal resection according to the operations 402-408 described with respect to FIG. 13.

A placing operation 504 places a femoral cutting guide on a condylar region of a patient femur. In one implementation, the femoral cutting guide includes a patient specific mating region, a distal resection slot, and a distal planar surface. The patient specific mating region is custom configured to interdigitate with a topography of the condylar region, and the patient specific mating region has surface contours that are a general negative image of surface contours of the condylar region. The distal resection slot includes an exterior opening defined in an exterior anterior surface of the femoral cutting guide, and the distal resection slot extends anterior-posterior and medial-lateral in the femoral cutting guide. The distal planar surface is generally parallel to the distal resection slot and distally spaced apart from the distal resection surface. In one implementation, the femoral cutting guide further includes a posterior resection slot configured to guide a posterior resection of the patient femur. In another implementation, the femoral cutting guide further includes a chamfer resection slot configured to guide a chamfer resection of the patient femur.

A causing operation 508 causes the patient specific mating region to interdigitate with the topography of the condylar region. With the patient specific mating region interdigitated with the topography of the condylar region, a checking operation 510 causes the distal planar surface of the femoral cutting guide to abut against the proximal resection made in the creating operation 502. The checking operation 510 checks a ligament balance of the patient knee with the femoral cutting guide engaged with the condylar region and the proximal resection.

A first making operation 512 makes a posterior resection of the patient femur via the posterior resection slot. A second making operation 514 makes a chamfer resection of the patient femur via the chamfer resection slot, and a third making operation 516 makes a distal resection of the patient femur via the distal resection slot. In one implementation, prior to the second making operation 514 and the third making operation 516, during which the chamfer and distal resections are performed, a distal pin is removed from the femoral cutting guide.

The discussion provided herein is given in the context of a unicompartmental knee arthroplasty cutting guides. However, the disclosure herein is readily applicable to other arthroplasty cutting guides as well as total or unicompartmental arthroplasty procedures in the knee or other joint contexts. Thus, the disclosure provided herein should be considered as encompassing cutting guides and the use thereof for both total and unicompartmental arthroplasty procedures. Additionally, the discussion given herein is applicable to cutting guides and methods applicable to restoring the patient to his or her natural alignment and also to cutting guides and methods applicable to arthroplasty procedures causing the patient's knee to be zero mechanical axis. Further, the discussion herein should be considered to encompass both medial and lateral unicompartmental cutting guides and arthroplasty procedures.

Various modifications and additions can be made to the exemplary embodiments discussed without departing from the spirit and scope of the presently disclosed technology. For example, while the embodiments described above refer to particular features, the scope of this disclosure also includes embodiments having different combinations of features and embodiments that do not include all of the described features. Accordingly, the scope of the presently disclosed technology is intended to embrace all such alternatives, modifications, and variations together with all equivalents thereof.

What is claimed is:

1. An arthroplasty cutting guide for making resections in a knee region of a patient femur in preparing a patient knee for the implantation of a femoral implant and a tibial implant, the knee region including surface topography including surface contours of a femoral condylar surface and a trochlear groove surface, the femoral implant including: an articular condylar surface; a femur contacting side opposite the articular condylar surface and including a distal resection contacting surface, a posterior resection contacting surface, and a chamfer resection contacting surface; and a first distal-proximal thickness extending perpendicular from the distal resection contacting surface to the articular condylar surface, the tibial implant including: an articular plateau surface; a tibia contacting side opposite the articular plateau surface and including a proximal resection contacting surface; and a second distal-proximal thickness extending perpendicular from the proximal resection contacting surface to the articular plateau surface, the arthroplasty cutting guide comprising:
 a patient specific mating region custom configured to interdigitate with the topography of the knee region and comprising surface contours that are a general negative image of the surface contours of the femoral condylar surface and the surface contours of the trochlear groove;
 a distal resection slot configured to guide a distal resection in the knee region when the patient specific mating region interdigitates with the topography of the knee region such that the surface contours of the mating region make corresponding surface contact with the surface contours of the femoral condylar surface and the trochlear groove; and
 a distal planar surface parallel to the distal resection slot and distally spaced apart from the distal resection slot by a distance equal to the sum of the first and second distal-proximal thicknesses.

2. The arthroplasty cutting guide of claim 1, further comprising a chamfer resection slot configured to guide a chamfer resection in the knee region when the patient specific mating region interdigitates with the topography of the knee region such that the surface contours of the mating region make corresponding surface contact with the surface contours of the femoral condylar surface and the trochlear groove.

3. The arthroplasty cutting guide of claim 2, further comprising a posterior resection slot configured to guide a posterior resection in the knee region when the patient specific mating region interdigitates with the topography of the knee region such that the surface contours of the mating region make corresponding surface contact with the surface contours of the femoral condylar surface and the trochlear groove.

4. The arthroplasty cutting guide of claim 1, further comprising a posterior resection slot configured to guide a posterior resection in the knee region when the patient specific mating region interdigitates with the topography of the knee region such that the surface contours of the mating region make corresponding surface contact with the surface contours of the femoral condylar surface and the trochlear groove.

5. The arthroplasty cutting guide of claim 1, further comprising a first pin hole extending through an anterior trochlear groove region of the mating region.

6. The arthroplasty cutting guide of claim 5, wherein the first pin hole extends in a direction generally parallel to the distal resection slot.

7. The arthroplasty cutting guide of claim 5, further comprising a second pin hole extending through a distal trochlear groove region of the mating region.

8. The arthroplasty cutting guide of claim 7, wherein the second pin hole extends in a direction generally canted relative to the distal resection slot.

9. The arthroplasty cutting guide of claim 5, further comprising a second pin hole extending through a distal condylar region of the mating region.

10. The guide of claim 9, wherein the second pin hole extends in a direction generally perpendicular relative to the distal resection slot.

\* \* \* \* \*